United States Patent
Geddes

(10) Patent No.: US 8,101,424 B2
(45) Date of Patent: Jan. 24, 2012

(54) BIOASSAYS USING PLASMONIC SCATTERING FROM NOBLE METAL NANOSTRUCTURES

(75) Inventor: Chris D. Geddes, Bel-Air, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 794 days.

(21) Appl. No.: 11/917,075

(22) PCT Filed: Jun. 15, 2006

(86) PCT No.: PCT/US2006/023156
§ 371 (c)(1),
(2), (4) Date: Jul. 21, 2008

(87) PCT Pub. No.: WO2007/053201
PCT Pub. Date: May 10, 2007

(65) Prior Publication Data
US 2010/0062545 A1 Mar. 11, 2010

Related U.S. Application Data

(60) Provisional application No. 60/712,711, filed on Aug. 30, 2005, provisional application No. 60/690,764, filed on Jun. 15, 2005.

(51) Int. Cl.
*G01N 21/00* (2006.01)
(52) U.S. Cl. ....... 436/164; 436/518; 436/525; 427/2.11; 427/10
(58) Field of Classification Search .................. None
See application file for complete search history.

(56) References Cited

U.S. PATENT DOCUMENTS

| | | | |
|---|---|---|---|
| 4,174,952 A * | 11/1979 | Cannell et al. ................ 436/534 |
| 4,766,083 A | 8/1988 | Miyashita et al. |
| 5,017,009 A | 5/1991 | Schutt et al. |
| 5,100,805 A | 3/1992 | Ziege et al. |
| 5,449,918 A | 9/1995 | Krull et al. |
| 5,866,433 A | 2/1999 | Schalkhammer et al. |
| 6,180,415 B1 | 1/2001 | Schultz et al. |
| 6,361,944 B1 | 3/2002 | Mirkin et al. |
| 7,253,452 B2 | 8/2007 | Steckel et al. |
| 7,348,182 B2 | 3/2008 | Martin et al. |
| 7,351,590 B2 | 4/2008 | Martin |
| 7,718,445 B2 | 5/2010 | Martin |
| 2001/0002316 A1 | 5/2001 | Hansen et al. |

(Continued)

FOREIGN PATENT DOCUMENTS

WO 89/09408 10/1989

(Continued)

OTHER PUBLICATIONS

Aslan et al., Nanogold plasmon resonance-based glucose sensing. 2. wavelength-ratiometric resonance light scattering, Feb. 2005, Analytical Chemistry 77: pp. 2007-2014.*

(Continued)

*Primary Examiner* — N. C. Yang
(74) *Attorney, Agent, or Firm* — Marianne Fuierer; Moore & Van Allen, PLLC

(57) ABSTRACT

The present invention relates to detecting and/or measuring scattering effects due to the aggregating metallic nanostructures or the interaction of plasmonic emissions from approaching metallic nanoparticles. The scattering effects may be measured at different angles, different wavelengths, changes in absorption and/or changes in polarization relative to changes in the distances between nanoparticles.

7 Claims, 17 Drawing Sheets

U.S. PATENT DOCUMENTS

| | | | |
|---|---|---|---|
| 2002/0161101 A1* | 10/2002 | Carroll et al. | 524/495 |
| 2003/0228682 A1 | 12/2003 | Lakowicz et al. | |
| 2004/0038264 A1 | 2/2004 | Souza et al. | |
| 2004/0072356 A1 | 4/2004 | Senisterra et al. | |
| 2004/0160606 A1 | 8/2004 | Lakowicz et al. | |
| 2006/0078998 A1* | 4/2006 | Puskas et al. | 436/64 |
| 2006/0147927 A1 | 7/2006 | Geddes et al. | |
| 2006/0256331 A1 | 11/2006 | Lakowicz et al. | |
| 2007/0020182 A1 | 1/2007 | Geddes et al. | |
| 2007/0269826 A1 | 11/2007 | Geddes | |
| 2008/0096281 A1 | 4/2008 | Geddes et al. | |
| 2008/0215122 A1 | 9/2008 | Geddes | |
| 2009/0004461 A1 | 1/2009 | Geddes et al. | |
| 2009/0022766 A1 | 1/2009 | Geddes | |

FOREIGN PATENT DOCUMENTS

| | | |
|---|---|---|
| WO | WO 2004/024191 | 3/2004 |
| WO | WO 2006/074130 | 7/2006 |
| WO | WO 2006/137945 | 12/2006 |
| WO | WO 2006/138698 | 12/2006 |
| WO | WO 2007/053201 | 5/2007 |

OTHER PUBLICATIONS

Aslan et al. (2005) Angular-Ratiometric Plasmon Resonance Based Light Scattering for Bioaffinity Sensing. J. Am. Chem. Society, 127:12115-12121.

Bryant, G.; Thomas, J.C. Improved Particle Size Distribution Measurements Using Multiangle Dynamic Light Scattering. *Langmuir* 1995, 11, 2480-2485.

Yguerabide, J.; Yguerabide, E. Light-Scattering Submicroscopic Particles as Highly Fluorescent Analogs and their Use as Tracer Labels in Clinical and Biological Applications. *Anal. Biochem.* 1998, 262, 137-156.

Aslan, K.; Lakowicz, J. R.; Geddes, C. D. Tunable plasmonic glucose sensing based on the dissociation of Con A-aggregated dextran-coated gold colloids. *Anal. Chem.Acta.* 2004, 517, 139-144.

Aslan, K.; Lakowicz, J. R.; Geddes, C. D. Nanogold-plasmon-resonance-based glucose sensing. *Anal. Biochem.* 2004, 330, 145-155.

Reynolds, R. A.; Mirkin, C. A.; Letsinger, R. L. Homogeneous, Nanoparticle Based Quantitative Colorimetric Detection of Oligonucleotides. *J. Am. Chem. Soc.* 2000, 122, 3795-3796.

Elghanian, R.; Storhoff, J.J.; Mucic, R.C.; Letsinger, R.L.; Mirkin, C.A. Selective colorimetric detection of polynucleotides based on the distance-dependant optical properties of gold nanoparticles. *Science* 1997, 277, 1078-1081.

Sastry, M.; Lala, N.; Patil, V.; Chavan, S.P.; Chittiboyina, A.G. Optical absorption study of the Biotin-Avidin interation on colloidal silver and gold particles. *Langmuir* 1998, 14, 4138-4142.

Cobbe, S.; Connolly, S.; Ryan, D.; Nagle, L.; Eritja, R.; Fitzmaurice, D. DNA-Controlled Assembly of Protein-Modified Gold Nanocrystals. *J. Phys. Chem. B* 2003, 107, 470-477.

Nath, N.; Chilkoti, A. A colorimetric gold nanoparticle sensor to interrogate biomolecular interactions in real time on a surface. *Anal. Chem.* 2002, 74, 504-509.

Souza, G.R.; Miller, J.H. Oligonucleotide detection using angle-dependent light scattering and fractal dimension analysis of gold-DNA aggregates. *J. Am. Chem. Soc.* 2001, 123, 6734-6735.

Mie, G. Contributions to the Optics of Turbid Media, Particularly of Colloidal Metal Solutions. *Ann. Phys.* 1908, 25, 377-445.

Collier, C.P.; Vossmeyer, T.; Heath, J.R. Nanocrystal Superlattices. *Annu. Rev. Phys. Chem.* 1998, 49, 371-404.

Roll, D.; Malicka, J.; Gryczynski, I.; Gryczynski, Z.; Lakowicz, J.R. Metallic Colloid Wavelength-Ratiometric Scattering Sensors. *Anal. Chem.* 2003, 75, 3108-3113.

Mayes, A. G.; Blyth, J.; Millington, R. B.; Lowe, C. R. Metal Ion-Sensitive Holographic Sensors. *Anal. Chem.* 2002, 74, 3649-3657.

Kim, Y.; Johnson, R. C.; Hupp, J. T. Gold Nanoparticle-Based Sensing of "Spectroscopically Silent" Heavy Metal Ions. *Nano Lett.* 2001, 1 (4), 165-167.

Millard, M.; Huang, P.; Brus, L. Silver Nanodisk Growth by Surface Plasmon Enhanced Photoreduction of Absorbed [Ag]. *Nano Lett.* 2003, 3, 1611-1615.

Finay, R. Particle Sizing by Quasi-Elastic Light Scattering. *Adv. Colloid Interface Sci.* 1994, 52, 79-143.

* cited by examiner

BIOASSAYS USING PLASMONIC SCATTERING FROM NOBLE METAL NANOSTRUCTURES

CROSS-REFERENCE TO RELATED APPLICATION

The present application claims priority to PCT Application No. PCT/US06/023156 filed in the U.S. Patent and Trademark Office, PCT Division, on Jun. 15, 2006, which in turn claims priority to U.S. Provisional Patent Application No. 60/690,764 filed on Jun. 15, 2005 and U.S. Provisional Patent Application No. 60/712,711 filed on Aug. 30, 2005, the contents of all applications are hereby incorporated by reference herein.

GOVERNMENT RIGHTS IN INVENTION

Work related to the invention was conducted in the performance of NIGMS/NIH GM070929. As a result of such contracts, the U.S. Government has certain rights in the invention described herein.

BACKGROUND OF THE INVENTION

1. Field of the Invention

The present invention relates to assay methods and systems, and more particularly, to assay systems and methods using plasmonic emissions generated by approaching or aggregating metallic surfaces.

2. Background of the Related Art

Dynamic Light Scattering (DLS), also referred to as photon correlation spectroscopy,[1] is the most widely used technique today for studying colloidal systems.[2-5] It is a relatively fast technique, which can provide absolute estimates of particle size and concentration for a wide variety of particles. However, the technique does have several limitations.[1] These limitations include the low information content from the measured signal, the complexity of data analysis (this involves the numerical inversion of a Laplace Transform[1]) and the fact that both DLS and the other scattering techniques are not appropriate for very dilute solutions of particles.[2-5] Subsequently, this has been a limitation in sensing biospecies at nanomolar and even lower concentrations.

Over the last several years, the use of both gold and silver nanoparticles in biological assays has dramatically increased. This has been afforded by their very high molar absorption coefficients,[6,7] which has enabled their use in many absorption-based (of light) nanoparticle assays.[8-14] In addition to their high absorption cross-sections, nanoparticles of gold and silver are also very efficient scatterers of light. Indeed a noble metal colloid's extinction spectrum is composed of both an absorption and scattering component, which is contrary to how a typical fluorophores extinction spectrum is understood. Subsequently, light scattering by gold and silver nanoparticles can be detected at concentrations as low as $10^{-16}$ M[6]. In addition, it is well known that the light dependent scattering properties of a nanoparticle depend on their size, shape, composition and the refractive index of the suspending medium.[6]

Typically, in cellular imaging today, fluorophores or even quantum dots, are used, which either contain some function groups to bind to expressed cellular surface features (receptors) or can even be transfected within the cells. This enables the cells to be readily imaged. However, one particular problem with using fluorophores is there inherent photo instability, where most fluorophores typically photo degrade after about $10^3$ excitation/emission event cycles. Thus, one constraint in immunosensing is the detectability of the fluorophore.

Notably, light scattering by metallic structures in known but heretofore several additional properties related to the light scattering from multiple metallic structures have been ill explored for biosensing applications. Thus, it would be advantageous to explore other scattering properties of nanoparticles and the interaction therebetween for affinity biosensing, including the spatial distribution of light scatter and its subsequent polarization dependence; and the ability of for noble metal nanostructures to dipole-couple over very large distances, thereby effectively breaking the fluorescence resonance energy transfer (FRET) limit imposed by current organic fluorophores.

SUMMARY OF THE INVENTION

Surface plasmons are collective oscillations of free electrons at metallic surfaces. These oscillations can give rise to the intense colors of solutions of plasmon resonance nanoparticles and/or intense scattering. When a metallic nanoparticle is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon scatter.[6]

Broadly the present invention relates to detecting and/or measuring scattering effects of plasmons from the surface of a metallic particle or from the interaction of plasmonic emissions from numerous approaching or aggregating metallic nanostructures. The scattering effects may be measured at different angles, different wavelength, changes in absorption and/or changes in polarization relative to changes in the distances between nanoparticles.

Notably, nanostructures are far superior to fluorophores in that they don't photodegrade and have far greater emissions than that of fluorophores. Further, nanostructures of gold and silver are very efficient scatterers of light.

In one aspect, the present invention relates to the use of surface plasmons in a biosensing method for measuring concentration of an analyte that induces colloidal aggregation, the method comprising:

(a) measuring the change in intensity of scattered light from small colloids relative to the intensity of scattered light measured for larger colloidal aggregates, wherein the intensity of the scattered light is measured at two angles relative to the incident light and a ratio is determined between the measured values of the two angles, and wherein the ratio decreases as aggregation increases.

In another aspect, the present invention relates to a biosensing method for measuring concentration of an analyte that induces colloidal aggregation, the method comprising:

(a) preparing metallic nanostructures comprising a noble metal and at least partially coated with a binding component having an affinity for the analyte, and wherein the colloids are at size that scatters light according to the Rayleigh theory;

(b) exposing the metallic nanostructures with electromagnetic radiation at a frequency that is absorbed and scattered;

(c) measuring the intensity of scattered light from the metallic nanostructures, wherein the intensity of the scattered light is measured at two angles relative to the incident light;

(d) contacting the metallic nanostructures with an analyte that has an affinity for the binding component; measuring the intensity of scattered light emitted from the metallic nanostructures, wherein the intensity of the scattered light is measured at the same two angles as in step (c); and (e) determining a ratio between the measured intensity values at the two angles, wherein the ratio approaches unity as aggregation increases.

Preferably, the angles for measuring intensities include angle ranges from 30 to 175 degrees for one angle and from 185 to 350 degrees for the second angle, and more preferably from 40 to 160 degrees and 200 to 320 degrees, and most preferably from 70 to 120 degrees and 230 to 300. The electromagnetic radiation is preferably applied by a monochromatic laser light at a frequency similar to plasmon absorption maxima of the colloids.

Preferably, the metallic nanostructures take the form of metallic particles having any geometric shape such as triangular, elliptical, spheres; metallic islands or colloids; and/or porous matrix. In the alternative a continuous or semicontinuous metallic surface may be used. The metallic element may include any form of a noble metal such as silver, gold, platinum, copper or a combination thereof, and more preferably the metallic material is gold or silver.

In a still further aspect, the present invention relates to using the emissions, due to the coupling of long range plasmonic scattering, from metallic nanostructures to replace typically used fluorescence probes, thereby overcoming the shortcoming of fluorophores.

Another aspect of the present invention relates to a bioassay for measuring concentration of receptor-ligand binding, the method comprising:

(a) preparing metallic nanostructures immobilized on a surface wherein the metallic nanostructures have positioned thereon a receptor molecule having affinity for the ligand;

(b) contacting the metallic nanostructures attached to the receptor molecule with a sample suspected of comprising the ligand of interest, wherein any ligand in the sample will bind to the receptor molecule to form a receptor-ligand complex;

(c) contacting the receptor-ligand complex with a detector molecule having affinity for the ligand to form a receptor-ligand-detector complex, wherein the detector molecule is attached to a metallic nanostructure, and wherein binding of the ligand to the receptor forms a metal complex comprising metallic nanostructures on opposing ends of receptor-ligand-detector molecule complex;

(d) exposing the metal complex to electromagnetic radiation at a frequency that is at least scattered by the metallic nanostructures; and (e) measuring an effect of coupling of plasmon scatter from the metallic nanostructures of the metal complex, wherein the effect comprises spectral shifts of wavelength absorption due to long range plasmon coupling from the two opposing metallic nanostructures, the ratio of scattered intensities from coupling of the long-range plasmon scatter at two different wavelengths and/or the reduction in polarization of the coupling of the long range plasmon scatter when the metallic nanostructure move to close proximity.

A still further aspect of the present invention relates to a sensing platform for measuring the polarization of scattered light of plasmonic emissions from the metal complexes, wherein the polarization value is decreased as the aggregation of the metal complexes increases. Further, the sensing platform may include measuring the change in intensity of long range plasmon scattered light at two angles relative to the incident light and a ratio is determined between the measured values of the two angles, and wherein the ratio decreases as aggregation of metallic nanostructures increases.

Yet another aspect of the present invention relates to a biosensing method for measuring concentration of an analyte, the method comprising:

(a) preparing metallic nanostructures immobilized on a surface wherein the metallic nanostructures are attached to a capture molecule having affinity for the analyte, and wherein the metallic nanostructures are sized to scatter light according to the Rayleigh theory;

(b) exposing the metallic nanostructures and capture molecule with electromagnetic radiation at a frequency that is absorbed and/or scattered by the metallic nanostructures;

(c) measuring the intensity of scattered light, wherein the intensity of the scattered light is measured at two angles relative to the incident light;

(d) contacting the capture molecule with a sample suspected of comprising the analyte of interest, wherein any analyte of interest in the sample will bind to the capture molecule to form a capture-analyte complex;

(e) contacting the capture-analyte complex with a detector molecule having affinity for the analyte to form a capture-analyte-detector complex, wherein the detector molecule is attached to a metallic nanostructure to form a metal complex comprising metallic nanostructures on opposing ends of capture-analyte-detector molecule complex;

(f) measuring the intensity of scattered light from formed metal complexes, wherein the intensity of the scattered light is measured at the same two angles as in step (c); and (g) determining a ratio between the measured intensity values at the two angles, wherein the ratio approaches unity as aggregation increases.

In as still further aspect the present invention relates to a biosensing method for measuring concentration of an analyte, the method comprising:

(a) preparing metallic nanostructures immobilized on a surface or free in solution wherein the metallic nanostructures have positioned thereon a capture/receptor molecule having affinity for the ligand;

(b) exposing the metallic nanostructures and capture/receptor molecule with electromagnetic radiation at a frequency that is absorbed and scattered by the metallic nanostructures;

(c) measuring the absorption intensity and wavelength of scattered light;

(d) contacting the metallic nanostructures attached to the capture/receptor molecule with a sample suspected of comprising the ligand of interest, wherein the ligand in the sample will bind to the capture/receptor molecule to form a capture/receptor-ligand complex;

(e) contacting the capture/receptor-ligand complex with a detector molecule having affinity for the ligand to form a capture/receptor-ligand-detector complex, wherein the detector molecule is attached to a metallic nanostructure to form a metal complex comprising metallic nanostructures on opposing ends of the capture/receptor-ligand-detector molecule complex;

(f) measuring the absorption intensity and wavelength of scattered light from formed metal complexes; and (g) determining the spectral shift in absorption wavelength, which is shifted as aggregation increases.

In a still further aspect, the present invention relates to an assay using High Throughput Screening (HTS), the method comprising:

(a) providing a well plate used in HTS systems comprising a multiplicity of wells;

(b) introducing metallic nanostructures into the wells, wherein the metallic nanostructures are coupled to a binding receptor having affinity for a target molecule (c) introducing at solution suspected of including the target molecule for binding to the binding receptor;

(d) introducing a detection molecule having affinity for the target molecule, wherein the detection molecule comprises a complement metallic nanostructure, wherein the complement metallic nanostructure will be positioned traverse to the metallic nanostructure on binding of the target molecule to the detection molecule;

(e) applying electromagnetic energy; and (f) measuring the plasmonic emissions from the system.

A further aspect of the present invention, relates to a kit for detecting a target molecule in a sample, the kit comprising (a) a container comprising a layer of immobilized metal particles deposited on a substrate fabricated of a polymeric or quartz material, wherein an immobilized probe is connected to the metal particles and wherein the immobilized probe has an affinity for the target molecule; and (b) a detector molecule having an affinity for the target molecule, wherein the detector molecule comprises a metallic nanostructure and wherein the binding of the target molecule to both the immobilized probe and detector molecule causes the two metallic nanostructures to be positioned at a distance sufficient for coupling of the plasmonic emissions from the metallic nanostructure for subsequent measuring.

Other features and advantages of the invention will be apparent from the following detailed description, drawings and claims.

DETAILED DESCRIPTION OF THE INVENTION

Figure 1:
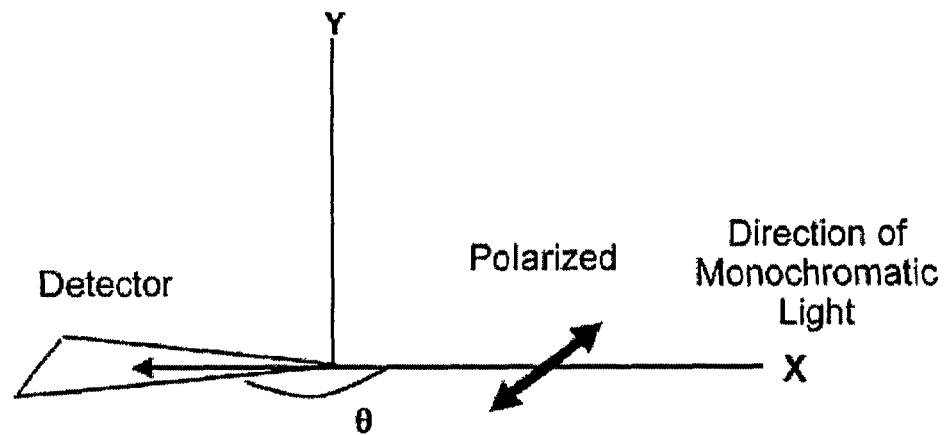
FIG. 1 shows the coordinate system used to describe the geometrical arrangement of the illumination and detection systems (Top), and the apparatus used for measuring the angular dependence of colloidal scatter (Bottom).
Figure 1:
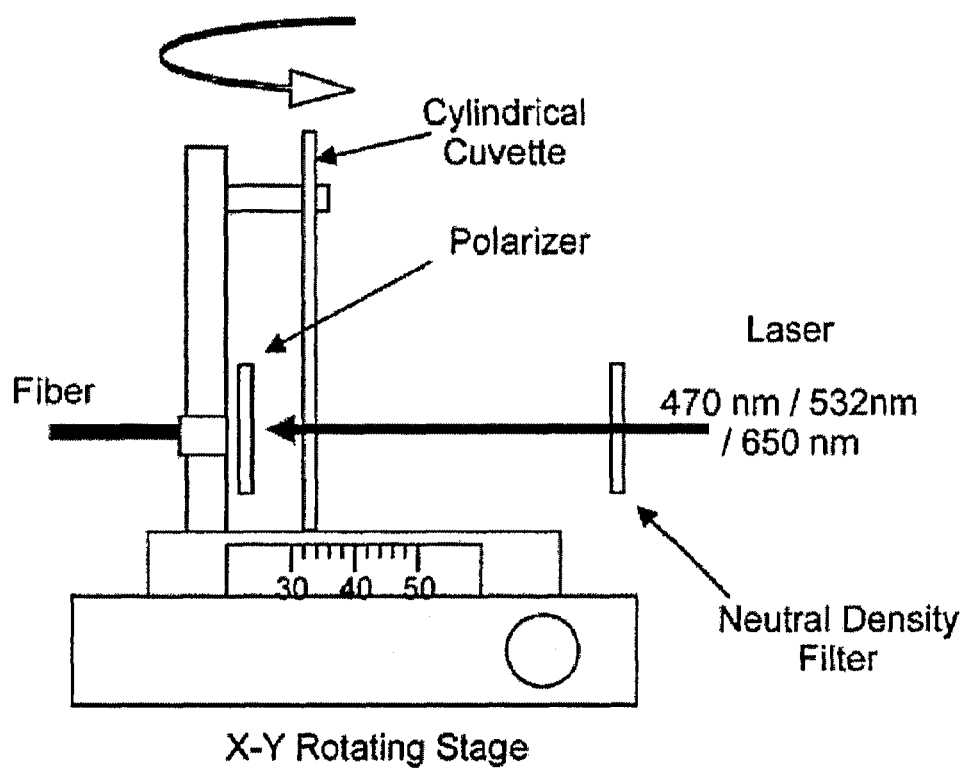

The present invention relates to affinity biosensing using plasmon light scattering emissions from interacting metallic nanoparticles.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

The present invention provides enhanced emissions using metallized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart.

Further, the metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

Light sources used for applying electromagnetic energy can include any source that may apply the necessary frequency or wavelength such as arc lamps and lasers. Detectors can include photomultiplier tubes. Additionally, it is advantageous for the device to have a monochromator so that specific wavelengths of light may be used to excite a molecule or to detect emissions at a specific wavelength.

In one embodiment the metallic particle may be prepared by reduction of metal ions using various reducing agents, using technique known to one skilled in the art. For example, sodium hydroxide may be added to a rapidly stirred silver nitrate solution forming a brown precipitate. Then ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Colloids can be prepared as suspensions by citrate reduction metals. Preferred metals are silver and gold. Again, gold may be used because of the absorption of gold at shorter wavelengths. The size of the colloids and their homogeneity can be determined by the extensive publications on the optical properties of metal particles available and the effects of interface chemistry on the optical property of colloids.

Silver island films can be formed by a chemical reduction of a silver salt on the quartz surface, which are relatively simple to fabricate.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity. Positioning of the biomolecule or metal particle at a desired distance can be achieved by using a film. The film may be a polymer film, a Langmuir-Blodgett film or an oxide film.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

In one embodiment, the application of low level microwave heating of the sample may be used to speed up any biological/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the low density silver metal, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metal nanoparticles in addition to the heating of any surface polar molecules. Intuitively, this leads to localized heating around the silver nanostructures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Figure 17:
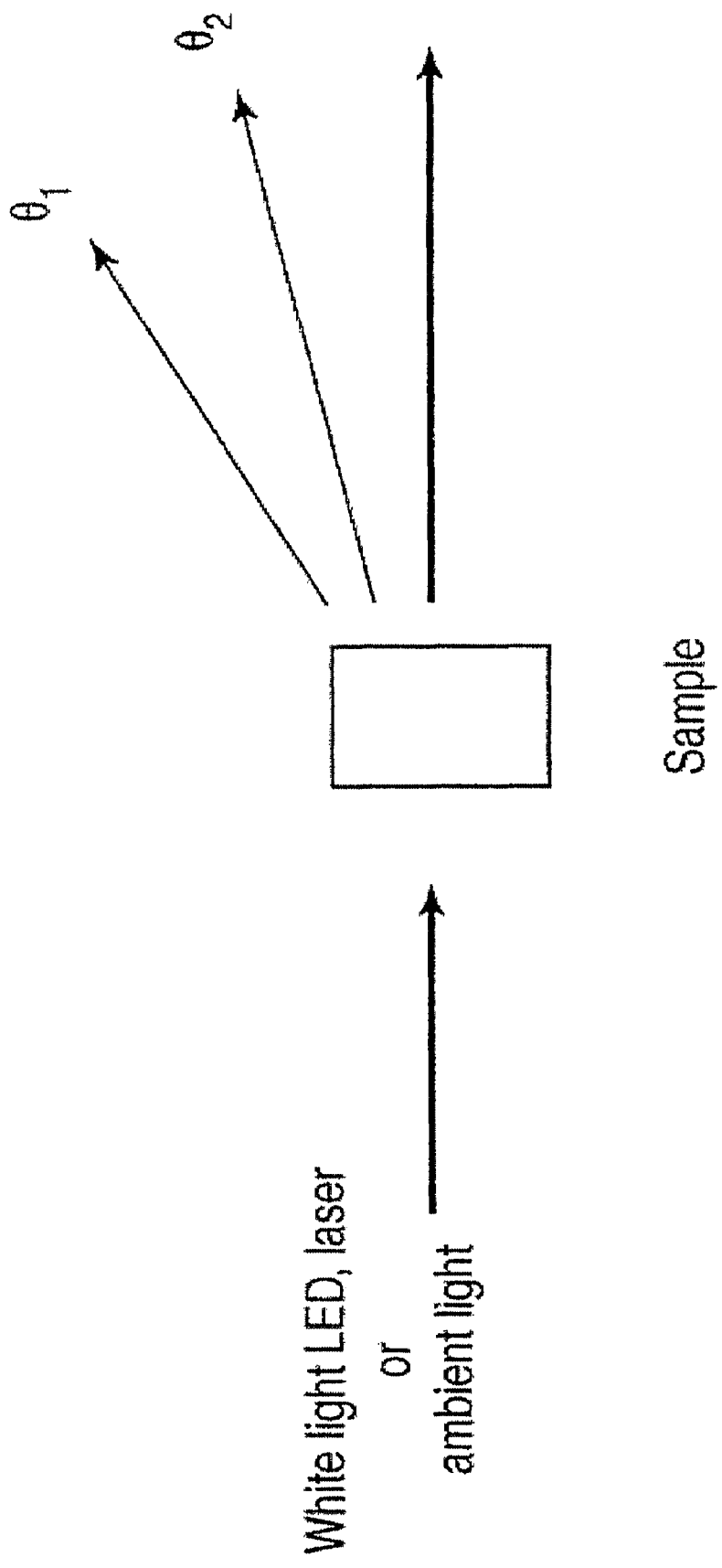
FIG. 17 shows the change in angular dependence of scatter upon a bioaffinity induced aggregation.

One embodiment relates to a ratiometric approach to the angular-dependent light scattering from bioactivated and subsequently aggregated noble metal colloids. This new sensing system utilizes the changes in particle scattering from very small colloids, which scatter light according to traditional Rayleigh theory, as compared to the changes in scattering observed by much larger colloidal aggregates, formed due to a bioaffinity reaction. These larger aggregates no longer scatter incident light in a $Cos^2\theta$ dependence, as is the case for Rayleigh scattering, but instead scatter light in a direction different from the incident geometry, as shown in FIG. 17. By subsequently taking the ratio of the scattered intensity at two angles, such as from 40 to 160 degrees and 200 to 320 degrees, relative to the incident light, the association of metallic particles may be followed when crosslinking agent is introduced.

As described above, horizontally polarized illumination of colloids demonstrates a $Cos^2\theta$ dependence of plasmon scatter in the same plane for particles that scatter in the Rayleigh limit. As shown in FIG. 17, 20 nm particles, which initially scatter in the Rayleigh limit, change their angular dependence of scatter upon a bioaffinity induced aggregation. Subsequently, the extent of forward scatter (180° with respect to the excitation) significantly increases as the particles no longer purely scatter in a $Cos^2\theta$ dependence, but indeed scatter in the Mie limit. By taking the ratio of scattered intensities at two arbitrary wavelengths, one can readily follow a bioaffinity reaction. Interestingly, the dynamic sensing range is extended by both choosing to measure one scattered intensity at 90°, while also choosing particles that are initially pure Rayleigh scatterers. Additionally, the measurements are independent of total nanoparticle concentration, which is not the case for other techniques such as dynamic light scattering. These findings suggest a very simple approach for field deployable biosensors; using either LEDs or ambient room light, the observer simply takes the ratio of the scattered intensity at two angles to determine the concentration of the biospecies of interest This new model system can be potentially applied to many other nanoparticle assays and has many advantages over traditional fluorescence sensing and indeed light-scattering approaches. For example, a single nanoparticle can have the equivalent scattered intensity as $10^5$ fluorescing fluorescein molecules substantially increasing detection; the angular distribution of scattered light from noble metal colloids is substantially easier to predict as compared to fluorescence; the scattered light is not quenched by biospecies; the ratiometric measurements described here are not dependent on colloid concentration as are other scattering techniques, and finally, the noble metal colloids are not prone to photodestruction, as is the case with organic fluorophores.

When a metallic nanoparticle is exposed to an electromagnetic wave, the electrons in the metal (plasmons) oscillate at the same frequency as the incident wave.[6] Subsequently, the oscillating electrons radiate electromagnetic radiation with the same frequency as the oscillating electrons. It is this reradiation of light at the same incident wavelength, which is often referred to as plasmon scatter.[6] The scattering of light by very small subwavelength sized particles, is well described by Rayleigh theory.[16] For incident light traveling along the x-axis, FIG. 1—top, and polarized in the y axis, the intensity of light scattered, $I_{scatt}$ in the direction $\theta$ by a homogeneous spherical particle with radius $\alpha$, that is much smaller than the wavelength, $\lambda$, of the incident beam, is given by the Rayleigh expression,[6,16]

$$I_{scatt} = \frac{16\pi^4 a^6 n_{mod}^4 I_0}{r^2 \lambda^4} \left|\frac{m^2-1}{m^2+2}\right|^2 Cos^2\vartheta \quad (1)$$

where $I_0$ is the incident intensity of monochromatic light, $n_{med}$ is the refractive index surrounding the particle, m is the refractive index of the bulk particle material and r is the distance between the particles and where the scattered light is detected. From FIG. 1—top the scattered light lies in the xy plane and is 100% polarized. Interestingly from FIG. 1 and Equation 1, the scattered light intensity is highest at the observation angles $\theta=0°$ and 180°, is zero at $\theta=90°$ and 270°, and is proportional to $Cos^2\theta$ at all other angles. This spatial or angular distribution of plasmon scatter is characteristic of an electric dipole emitter.[6] Equation 1 is ideally suited for single particle scattering or for particle suspensions where the particles are sufficiently spaced so that interpretable perturbations and multiple scatterings are insignificant. For very dilute samples of multiple particles, where the absorbance of the incident wavelength is less than $0.005^6$ then the intensity of the scattered light can be obtained by multiplying the single particle scattering intensity expressions by the particle concentration, p, (particles/cm$^3$). The intensity is therefore proportional to the nanoparticle concentration and the dilute solution has same angular distribution of scatter, and degree of polarization, as an individual "Rayleigh particle."[6] However, for larger particles, where the size of the nanoparticle is ~greater than $\frac{1}{20}^{th}$ the wavelength of light, or for Rayleigh sized particles in close proximity to one another, the scattering properties no longer obey Rayleigh theory, but indeed can be described by Mie's theory.[17] The angular dependence of plasmonic scatter subsequently changes from the $Cos^2\theta$ dependence described by Equation 1 (Rayleigh limit), to a much more complex spatial distribution of scatter, where the degree of forward scatter (i.e. 180° in our geometry, FIG. 1), increases with particle size (Mie limit).[17]

It is informative to briefly describe why the scattering from larger particles is no longer described by Rayleigh theory. It was previously mentioned that when a small particle is exposed to an electromagnetic field, whose wavelength is much larger than the diameter of the particle, then the electrons in the nanoparticle all sense the same phase of the incident wave, and therefore all scatter light with the same phase. In essence, the whole particle behaves as a large oscillating dipole moment, a function of the collective electron oscillations (plasmons). However, for much larger particles then the electrons on the particles can experience different phases, and therefore can oscillate with different phases. This inherently leads to interference of the light, which is scattered by the electrons from different parts of the particles. Subsequently, both the magnitude and angular distribution of the scattered light deviate from that expected of a normal oscillating electric dipole. The Mie theory for light scattering from large particles can be considered as light radiating from oscillating electric dipoles, as well as magnetic dipoles, quadruples and other higher order magnetic multipoles.[17] Scattered light by Mie theory is well known and described by the following equation;[f]

$$I_{scatt} = \frac{2\pi}{k^2}\sum_{n=1}^{\infty}(2n+1)(|a_n|^2+|b_n|^2) \quad (2)$$

where $k=2\pi n_{med}/\lambda$. One can envision the different terms in the sum as corresponding to different electric and magnetic multipoles and n is the term index. The term with n=1 corresponds to the electric dipole. The coefficients an and bn are defined in terms of the Bessel and Ricatti functions and in general are complex numbers depending on whether the refractive index of the particle is real or complex[6]. When the particle is much smaller than the wavelength of light, the most important expression in the Mie equation becomes that of the electric dipole, and then the Mie equation reduces back to the Rayleigh expression.

Figure 7:
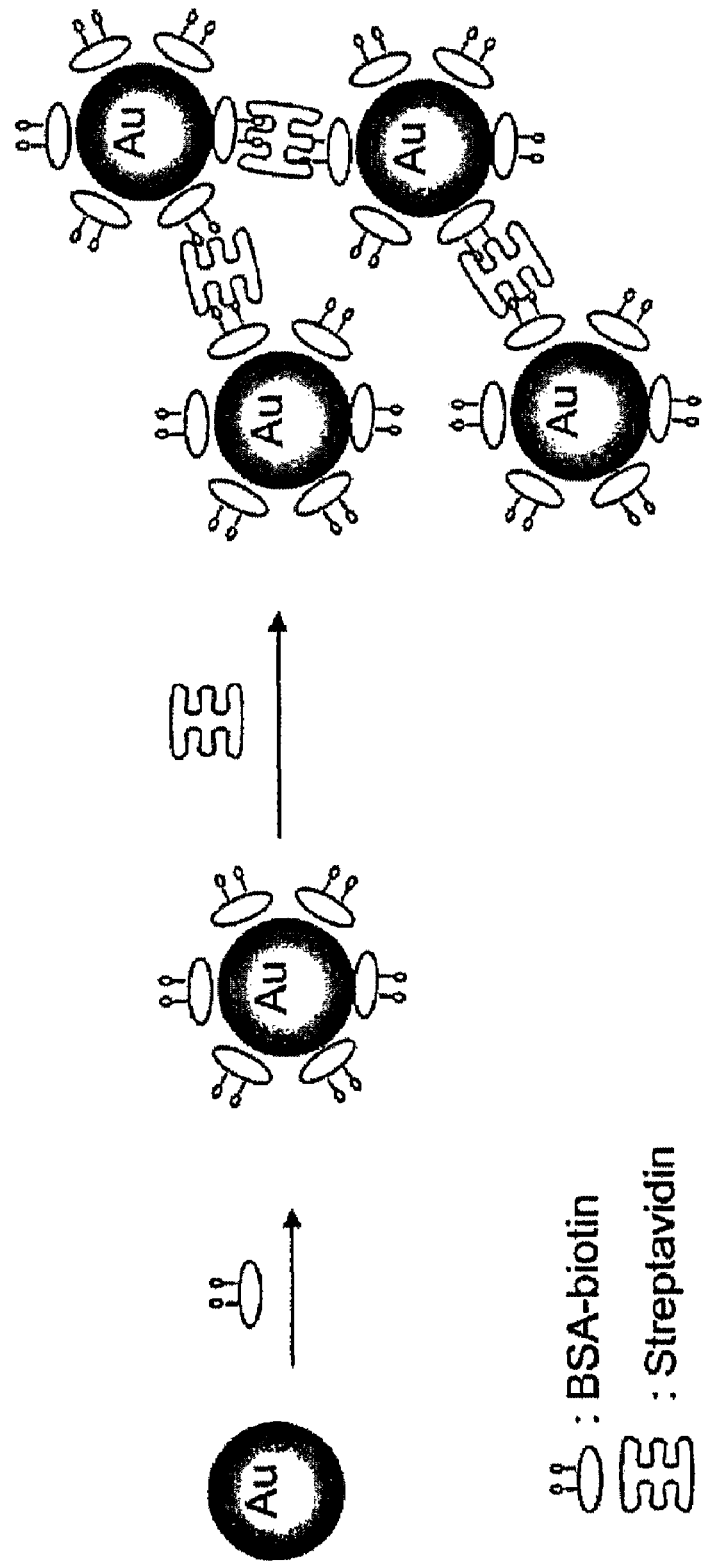
FIG. 7 shows a model system (BSA-Biotin colloids crosslinked by streptavidin) to demonstrate the utility of Angular-Ratiometric Plasmon-Resonance based light scattering for affinity biosensing.

To demonstrate the utility of this new sensing approach, the angular dependence of laser-light scatter from different sized gold colloids is demonstrated herein. These colloids range in size from 20-200 nm, where the differences in their angular distribution of scatter serve to confirm and support the bioaffinity solution based assay of the present invention, where small nanoparticles aggregate into much larger structures using a crosslinking agent that facilitates such aggregation, such as shown in FIG. 7.

The angular distribution (spatial distribution) of scatter from different sized colloids is known to be markedly different,[6] but heretofore has never been utilized for sensing. For small particles whose diameters are less than 1/20$^{th}$ the wavelength of light, the scatter of light is described well by Rayleigh theory,[6,16] where as the Mie theory[17] describes the scattering from the much larger structures. It is shown herein that the $Cos^2\theta$ dependence of scatter from small unaggregated particles in the Rayleigh limit, is no longer a valid description of the scattering distribution for much larger, aggregated particles. In this regard, unaggregated colloids (monomers) were chosen whose scatter can initially be well described by Rayleigh theory, but after protein induced aggregation, now resides in the Mie limit for scattering. As mentioned, the initial choice of nanoparticle size is paramount for the biosensing platform described in this paper. Rayleigh theory applies quite strictly to particles for which the radius $a<<<\lambda/(2\pi n_{med}|m|)$. For silver colloids and the wavelengths discussed here, $|m|$ is usually not greater than 4.[6] For $|m|=4$, $\lambda=532$ and 650 nm and $n_{med}=1.33$, this expression yields particles with radii of 15.9 and 19.4 nm respectively. According to Yguerabide,[6] particles up to about 40 nm are still considered to be in the Rayleigh limit. Subsequently for this work, 20 nm gold colloids were chosen, which can be purchased monodispersed from Ted Pella, CA, USA.

In addition to "breaking" the $Cos^2\theta$ angular dependence of Rayleigh scatter by protein aggregation of the nanoparticles as an approach to sensing, the ratio of the scattered intensities at different angles was determined, so that the measurements became independent of light fluctuations, background light and most importantly nanoparticle concentration, which is not the case with other light scattering techniques.[1-5] This subsequently allows the quantitative measurement of the concentration of protein in the model system, or potentially any species that induces nanoparticle aggregation. Thus, this angular-ratiometric plasmon-resonance based light scattering approach for bioaffinity sensing, will serve as a model system which could readily be applied to the many other nanoparticle assays which have been developed.[8-14]

To demonstrate the present sensing approach, whereby the angular dependence of plasmonic scatter changes upon colloidal aggregation induced by a bioaffinity reaction, the scattering behavior of uncoated gold colloid suspensions was initially studied. Notably, any noble metal may be used to fabricate the nanostructures of the present invention, as discussed hereinabove.

Figure 2:
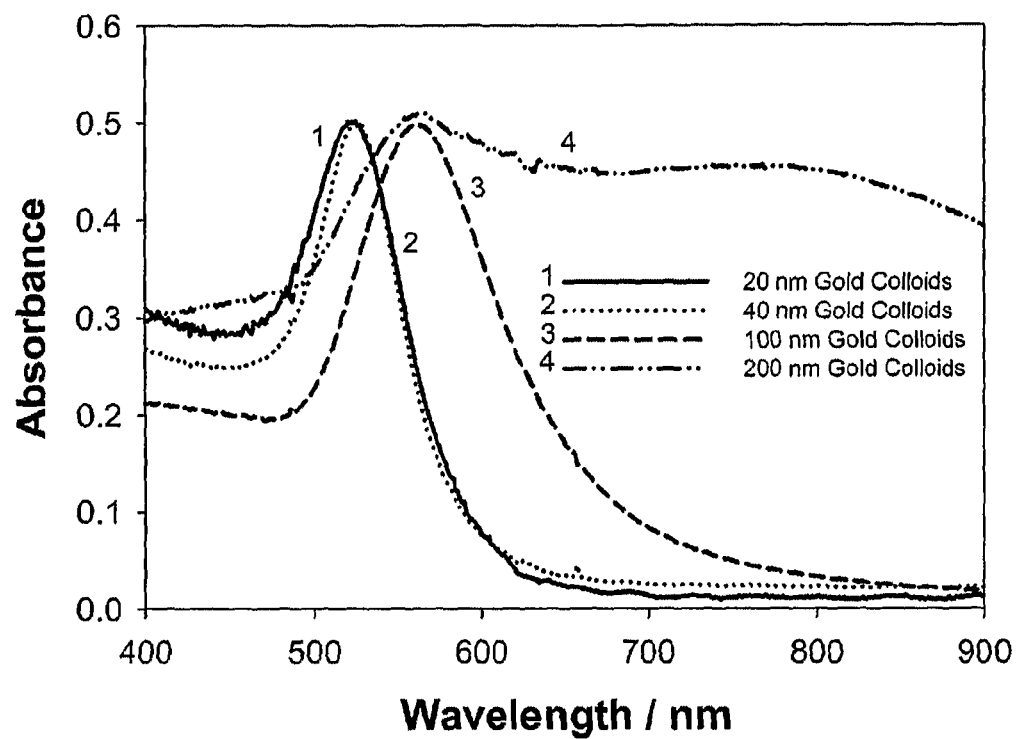
FIG. 2 shows the normalized absorption spectra of different sized gold colloids.

FIG. 2 shows the normalized absorption spectra of different sized gold colloids in citrate buffer. It can be clearly seen that the plasmon absorption band at 520 nm for 20 nm colloids, shifting red, as well as broadening as a function of size. Subsequently, for the angular scattering dependences discussed herein, monochromatic laser light at 470, 532 and 650 nm was used because these frequencies are similar to the plasmon absorption maxima of the colloids.[14,18]

Figure 3:
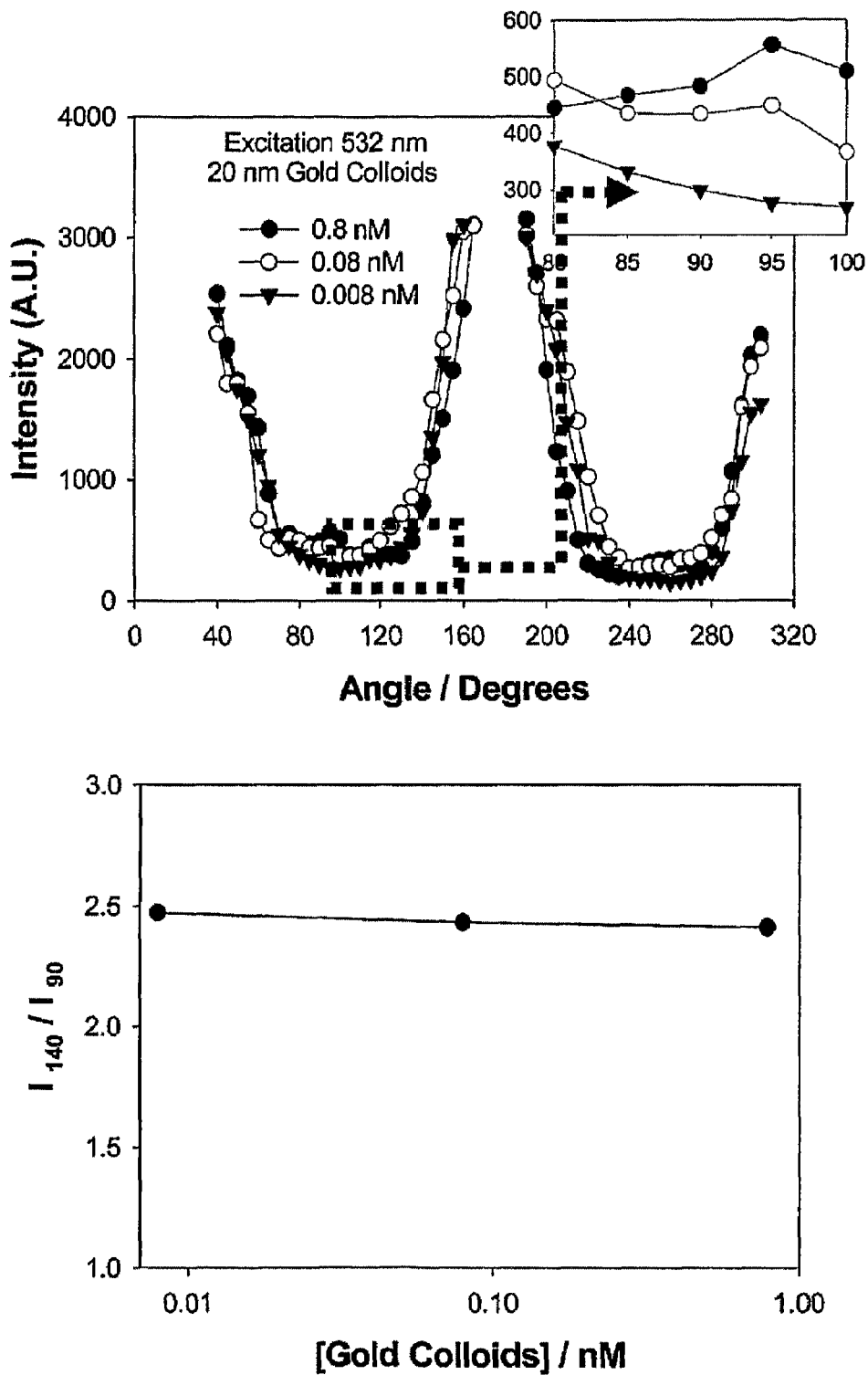
FIG. 3 shows the angular dependent scattering of 20 nm colloids using 532 nm laser light as a function of colloid concentration (Top), enlarged 80-100 degree region (Top insert) and the I140/I90 intensity ratio vs colloid concentration (Bottom).

For bioaffinity sensing based on the angular dependence of plasmon scatter, it is important to understand the concentration dependence of the colloids on the scattering spatial distribution. FIG. 3 shows the angular scattering profiles for different concentrations of 20 nm colloids using 532 nm monochromatic laser light. As predicted by equation 1, the $Cos^2\theta$ dependence on scattering can clearly be seen in these dilute samples. At angles approaching 0, 180 and 360 degrees, the scattering is the most pronounced, minimums in the scattering occurring at 90 and 270 degrees respectively. As expected the 2 sets of scattering curves in FIG. 3—top are mirror images of each other, and simply reflect the 0-180 and 180-360 degree regions, as the fiber optic detector is rotated around the samples, c.f. FIG. 1—bottom. Approaching 0, 180 and 360 degrees, the detector is rapidly saturated and hence the intensity values at 0, 180 and 360 degrees were not measurable. In fact, the dynamic range of scattering presented in FIG. 3—top is a compromise between the laser power used, and being able to detect both the minimum and maximum scattering intensities. Preferably, measurements are determined for scattering intensities at angles from 40 to 160 and 200 to 320 degrees.

Rayleigh theory for the scattering of light by dilute solutions of small colloids predicts that the scattering intensity at a given angle, increases as a function of colloid concentration. This can be clearly seen in FIG. 3—top insert, which is simply the enlarged 80-100 degree region. However, by taking the ratio of any two intensities, in this present situation 90 and 140 degrees, then the scattered intensities become independent of the colloid concentration. In addition, these angular ratiometric measurements are independent of excitation (light fluctuations) or detector drifts as well as background room light, notable features for biosensing.

FIG. 3—bottom indeed demonstrates this sensing strategy and shows an angular-ratiometric plot of intensities recorded at 140 and 90 degrees as a function of 20 nm gold colloid concentration. The linearity of the plot shows that the concentration of the colloids does not change the spatial distribution of the scatter, which is a most important consideration for sensing applications. In addition, the concentration range studied, typically reflects that used in colloidal plasmon absorption type biosensing assays[19-21].

Figure 4:
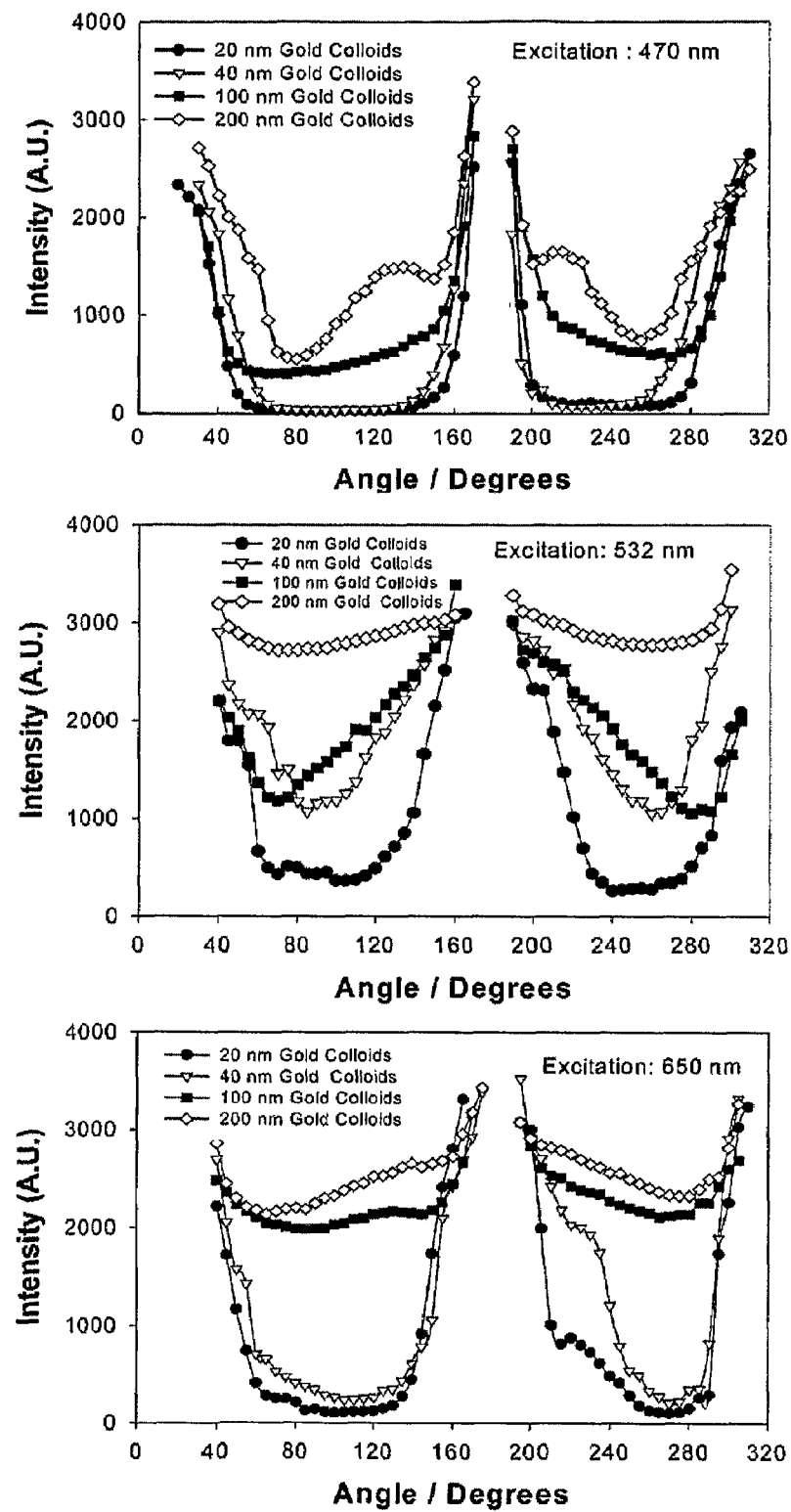
FIG. 4 shows the angular dependent scattering from 0.8 nM different sized gold colloids using 470 nm (Top), 532 nm (Middle) and 650 nm (Bottom) laser light.

FIG. 4 shows the angular dependent scattering from 0.8 nM different sized gold colloids using 470, 532 and 650 nm laser light, top to bottom respectively. There are two main features to these plots. Firstly, the colloidal size dependence of scattering at a given incident wavelength, and secondly, the differences in scattering distributions for a given colloid size using different incident wavelengths. At a given incident wavelength, all the plots show a size dependence on scattering distribution, FIG. 4. These results show that the scattering from 20 nm colloids typically follows a $Cos^2\theta$ dependence as depicted by Rayleigh theory, i.e. equation 1. As the colloidal size increases, the angular scattering profiles become much more complex and are no longer described by the Rayleigh expression but can indeed be described by Mie's theory[17]. In Mie's theory, the degree of forward scatter increases as the particle size increases.[17] From FIG. 4—middle, it can be clearly seen that the width of the scattering spectrum at 180 degrees increase as a function of colloidal size. In the presently described system, 180 degrees is the angle of forward scatter, as shown in FIG. 1 and FIG. 17.

Subsequently, by taking the ratio of the scattered intensities at different angles, such as 90 and 140 degrees as a function of gold colloid size, FIG. 5, it can be seen how the size distribution of scatter is changing. For small colloids, $I_{140}/I_{90}$ ratio is quite large, in the range 3-7, as the scattering follows a $Cos^2\theta$ dependence. However, for much larger colloids the discrete $Cos^2\theta$ scattering distributions are lost, the scattering no longer follows a $Cos^2\theta$ dependence and the ratio becomes close to unity, as shown in FIG. 5.

For the presently described bioaffinity sensing scheme, the initial gold colloid size was chosen so that it would be in the Rayleigh limit, i.e. within the range of 10 nm to 40 nm, and more preferably from about 20 nm to 30 nm. Upon affinity induced aggregation of the colloids, the scattering distributions become increasingly more complex as a function of protein addition, the scattering no longer following a Cos 2θ dependence. Similar to the unmodified colloids, the $I_{140}/I_{90}$ ratio changes, and can subsequently be correlated with protein concentration, or indeed any analyte or biospecies which can induced colloidal aggregation. Importantly, the dynamic range of the sensing strategy manifests itself in being able to aggregate particles that initially scatter in the Rayleigh limit, into the Mie limit after aggregation, c.f. the range shown in FIG. 5.

Figure 5:
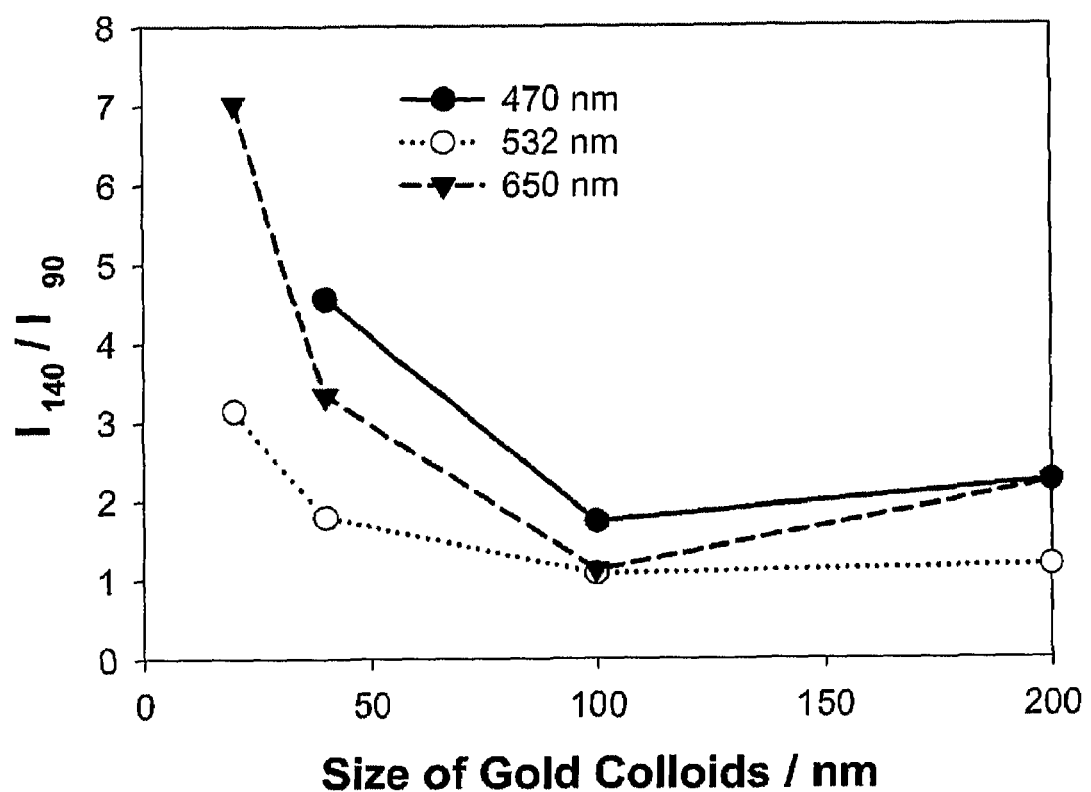
FIG. 5 shows the intensity ratio at 140 and 90 degrees vs. colloid size for 3 different incident wavelengths.

From FIGS. 4 and 5 it can be seen that the scattering distribution and therefore the $I_{140}/I_{90}$ ratio for a given colloid size changes with incident wavelength respectively. Unlike the colloidal size dependence for a fixed incident wavelength, these trends are much more complex to interpret and are due to both the absorption and scattering components of a colloid's extinction spectrum,[6] in addition to the position of the plasmon absorption maximum.[6,14,18] For the sensing scheme described herein, both 532 and 650 nm incident wavelengths were chosen. This is because 20 nm colloids have a plasmon absorption maxima at ~520 nm,[14-18] and the potential applications of this technology to biological sensing and the respective need to alleviate biological auto-fluorescence by using longer incident wavelengths.[22]

Figure 6:
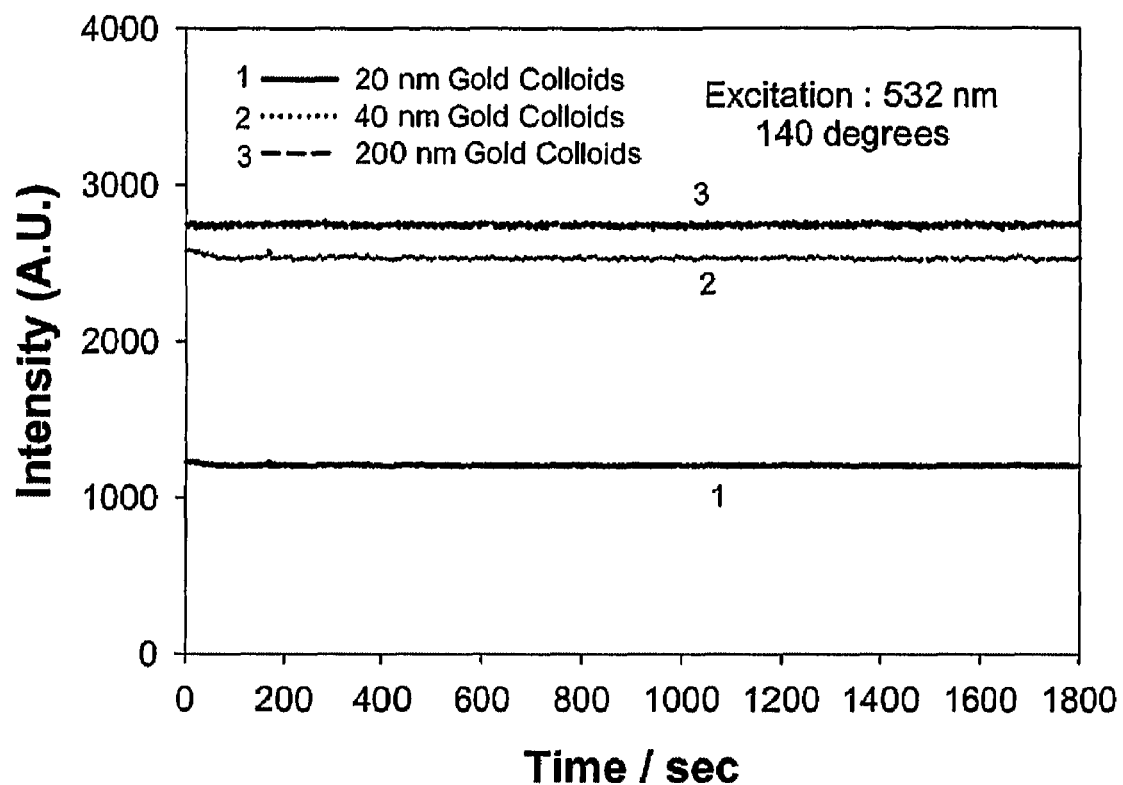
FIG. 6 shows the scattered intensity at 140 degrees for different sized colloids as a function of time using 532 nm laser light.

Finally, to investigate both the photostability of the colloids, as well as to ascertain whether the colloids would settle out of solution as a function of time, the scattering intensity was monitored as a function time using 532 nm incident light measured at 140 degrees and shown in FIG. 6. For all colloid sizes it was found that the intensity remained constant over the 30 minute measurement period. This was particularly encouraging and demonstrates that both the colloids do not settle from solution during measurements, and that the laser powers employed (several mW) do not alter the shape of the colloids, as has been reported by some authors, but for higher incident laser powers.[23] From FIG. 6, it can be seen that the colloids are photostable, more so than traditional fluorophores, which are prone to photo degradation,[22] their scattering distributions not changing as a function of time.

To demonstrate the utility of the described system, a model protein system was chosen as shown in FIG. 7. Biotinylated bovine-serum albumin-coated 20 nm colloids (BSA-colloids) can be readily prepared, which cluster by the addition of the tetravalent protein streptavidin,[19] and the association of biotin and streptavidin is very strong,[19] eliminating the possibility of back disassociation reactions to complicate our model system's kinetics.

Figure 8:
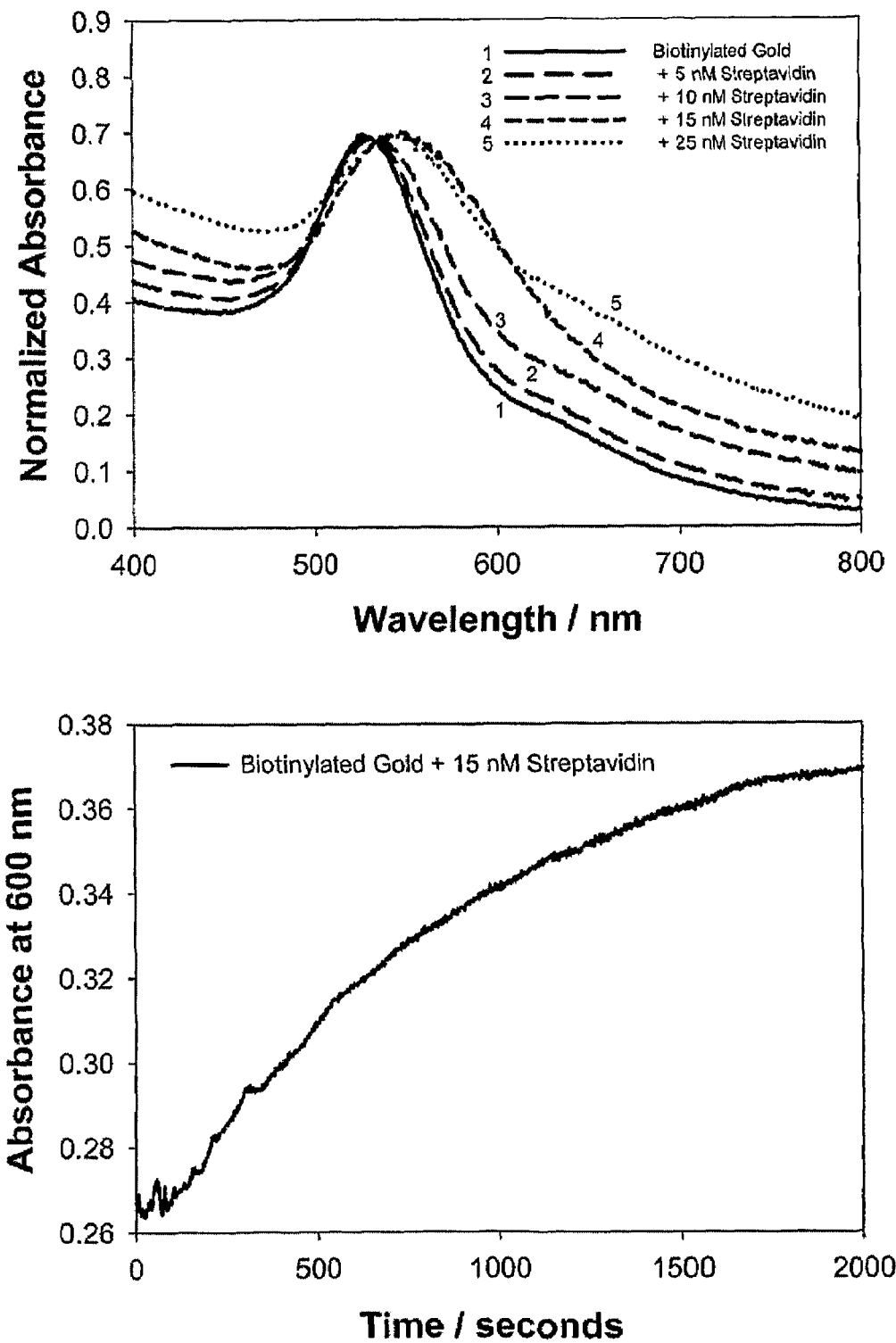
FIG. 8 shows the changes in absorption spectra of BSA-biotin colloids crosslinked by streptavidin (Top) and the time dependent change in absorption at 600 nm for a 15 nM streptavidin addition (Bottom).

FIG. 8—top shows the normalized absorption spectra of BSA-colloids as a function of streptavidin addition. The absorption spectra were taken after completion of the aggregation, which was typically 45 minutes for each sample. FIG. 8—bottom shows the time dependent change in absorption at 600 nm for a 15 nm streptavidin addition. After 2000 seconds, it can be seen that the reaction is essentially >90% complete.

Figure 9:
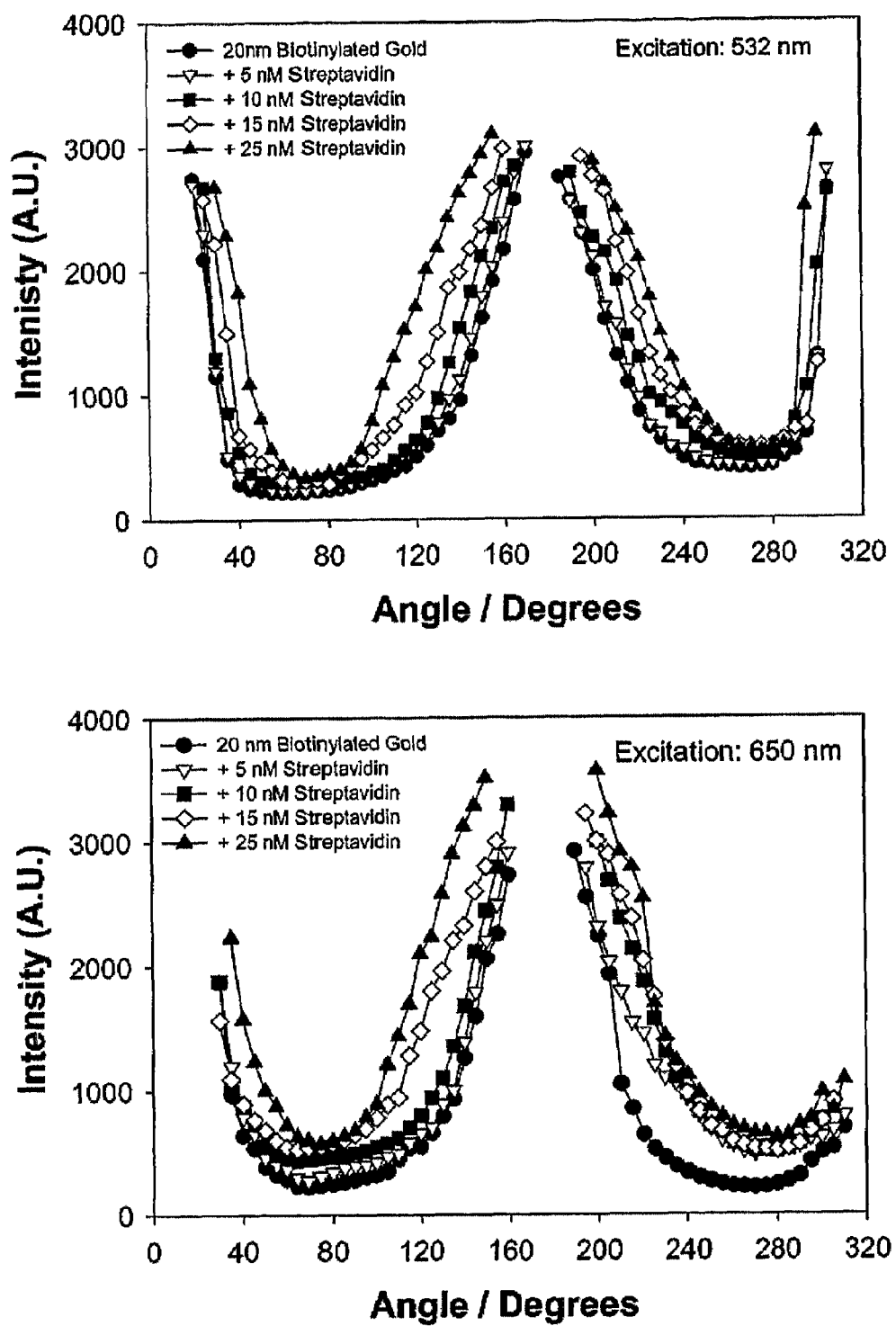
FIG. 9 shows the angular dependent scattering from 20 nm BSA-biotin colloids crosslinked by streptavidin from 532 nm (Top) and 650 nm laser light (Bottom).
Figure 10:
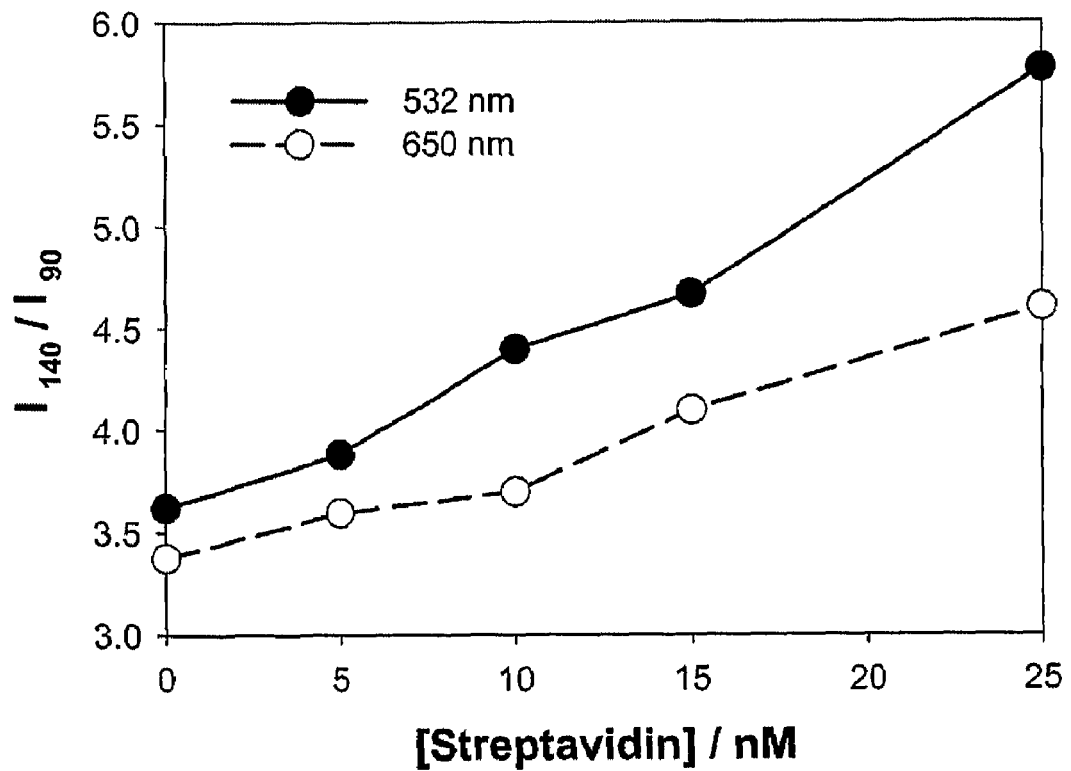
FIG. 10 shows the scattered intensity ratio of I140/I90 from aggregated BSA-biotin colloids for both 532 and 650 nm laser light as a function of streptavidin concentration.
Figure 11:
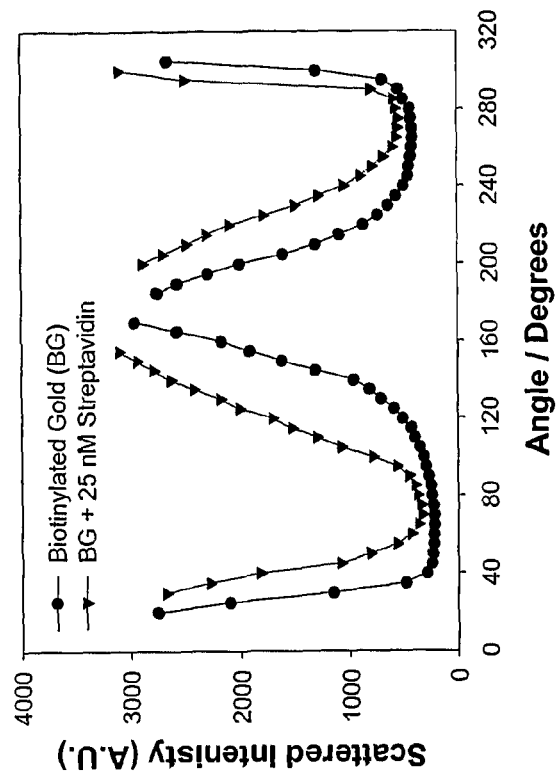
FIG. 11 shows a simplified view of the intensities values for a gold particle and the intensities due to colloidal aggregation showing that as aggregation increases the ratio approaches unity.
Figure 11:
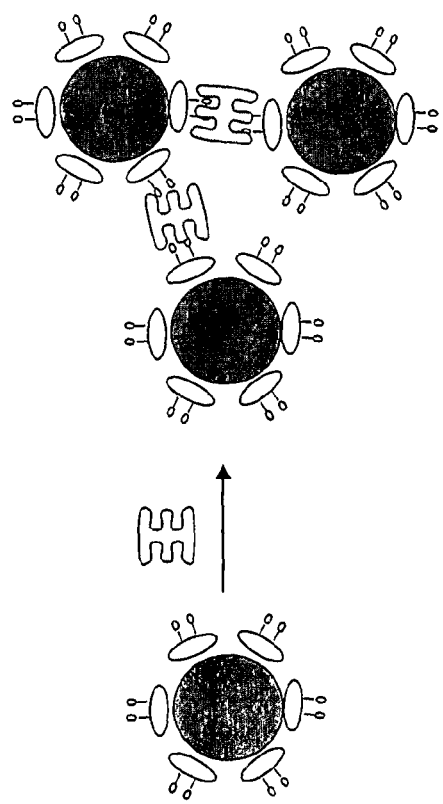

Identical concentration and compositions of BSA-colloids were subsequently incubated with different concentrations of streptavidin for 45 minutes, the angular scattering profiles then taken using both 532 (FIG. 9—top) and 650 nm (FIG. 9—bottom) incident light, in an analogous manner to the virgin colloids described earlier. From FIG. 9 it can be clearly see that the streptavidin induced association reaction changes the angular scattering profile from a relatively simple $Cos^2 θ$ dependence in the absence of streptavidin, to one much more complex, with a higher degree of forward scatter. These changes are consistent with a change in scattering from Rayleigh like particles to particles in the Mie limit as depicted by equations 1 and 2. Importantly, by taking the $I_{140}/I_{90}$ intensity ratio, the BSA-colloid association reaction was followed as a function of streptavidin addition as shown in FIG. 10. Using this model system, a notable change was observed in the $I_{140}/I_{90}$ intensity ratio using 532 and 650 nm incident light. While a relatively simple model system was chosen to demonstrate this sensing approach, this approach can be applied to monitor many other nanoparticle biological association/disassociation reactions.

Thus, one embodiment of the present sensing system includes a new approach to bioaffinity sensing wherein nanoparticles are used instead of fluorophores for sensing, and this approach provides advantages over other scattering-based techniques including:

simplification of instrumentation by using a laser and measuring the ratio of the scattered light intensity at two unique angles;

the ratio of the scattered intensity at two angles which is independent of nanoparticle concentration;

use of the metallic nanoparticle are not prone to photodestruction with the use of the intense illumination intensities in contrast to fluorophores; and the lifetime of plasmon scatter is usually less than 1 ps, where as fluorescence lifetimes are usually on a nanosecond timescale, as such, plasmon light scatter is not prone to quenching by biospecies, unlike many fluorophores.[6,22]

Figure 16:
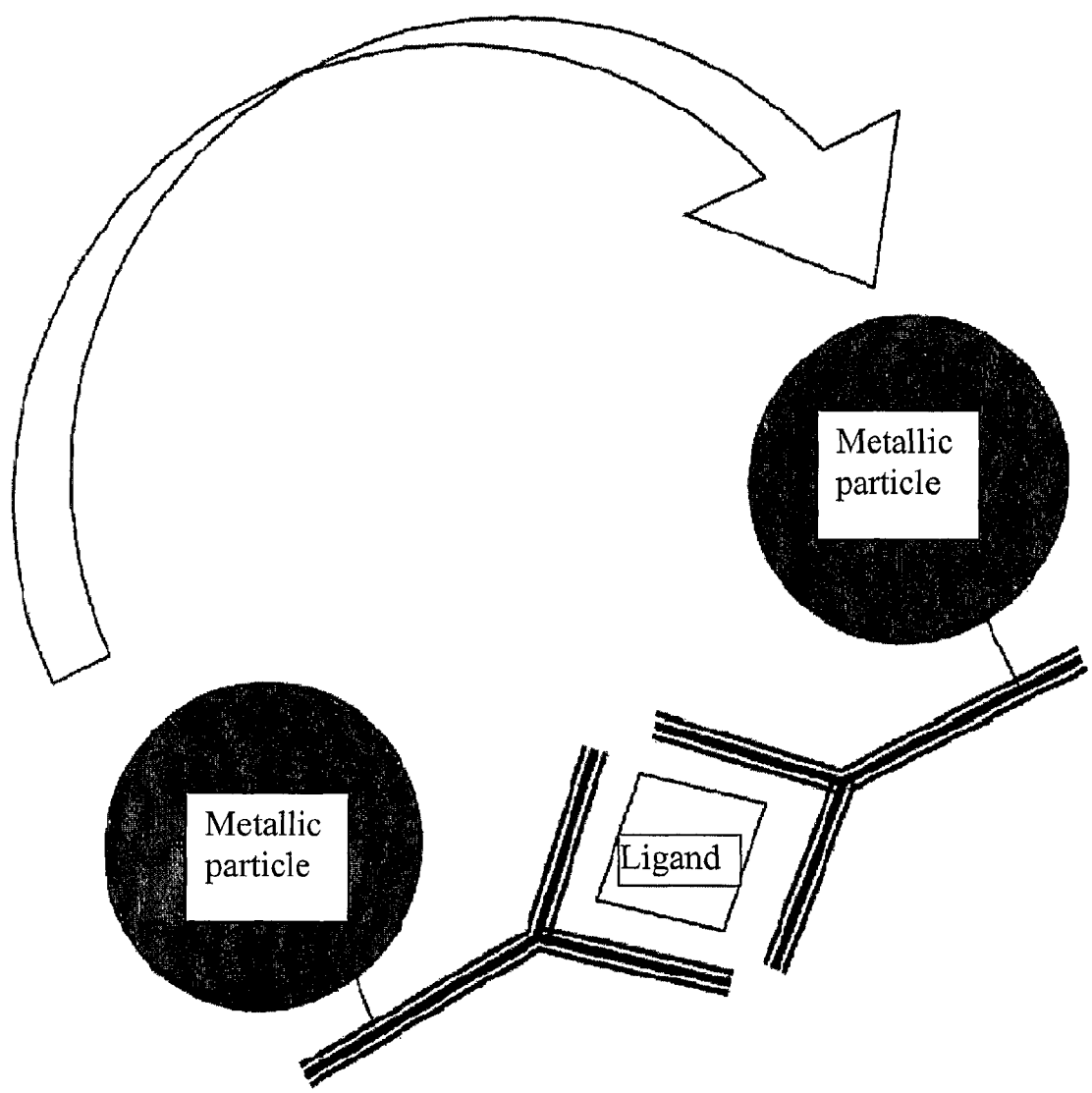
FIG. 16 shows long range plasmon coupling for sensing platforms.

In another embodiment, a receptor molecule may be fused to a noble metal nanostructure that can be free in solution or immobilized on a glass or polymeric smooth surface, wherein a ligand in a sample can bind to the receptor molecule. Importantly, instead of using a fluorescing detector biomolecule to bind to the ligand to determine presence of such a ligand in the assay, the present invention provides for a detector molecule that is attached to a metallic nanostructure and has affinity for the ligand at a position different from that of the receptor molecule. When the system is irradiated with electromagnetic energy, both the noble metal nanostructure and the metal on the detector molecule radiate long range plasmonic emissions that are coupled, as shown in FIG. 16 and can be subsequently measured using several different sensing platforms including measuring changes in plasmon absorption, intensity of scatter, angular dependence of scatter or polarization based scatter.

Figure 15:
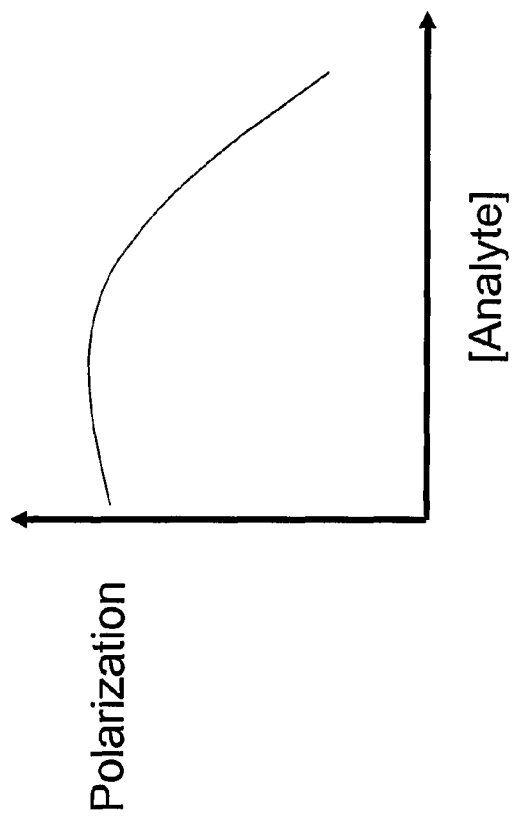
FIG. 15 shows the decrease in polarization as the analyte increases due to increase close proximity of the metallic structures.
Figure 15:
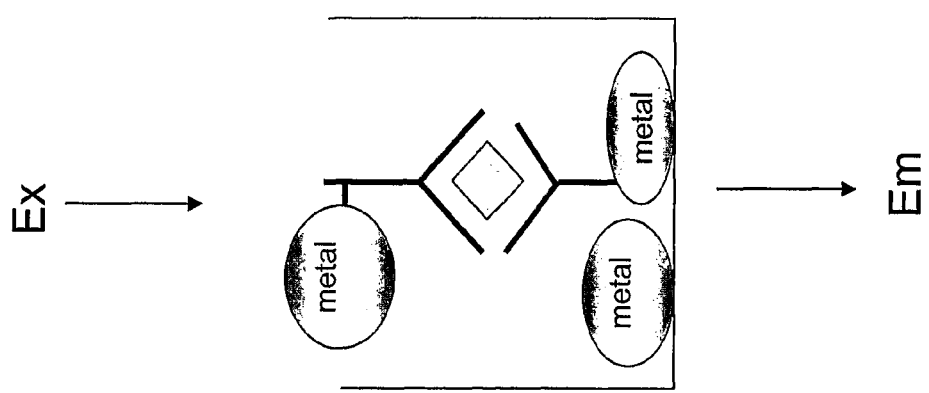

For example, when the two metal nanostructures approach, the polarization of plasmonic scatter changes due to metal aggregation induced by a bioaffinity reaction. The difference of the polarization of the coupled plasmonic scatter is compared to a control for non-aggregated nanostructures. As shown in FIG. 15, as the binding of ligand/analyte to the capture/receptor increases, the polarization decreases. Thus, this decrease in polarization can be used to determine the level of concentration of ligand/analyte when compared to a control system. As formation of the receptor-ligand-detector increases with aggregation of metallic nanostructures, the polarization decreases proportional to the concentration of binding ligand.

Upon aggregation of the nanoparticles, the solution polarization rapidly decreases due to near-field plasmon coupling. Interestingly, by choosing particles that initially scatter incident light in a Rayleigh manner, the present inventor has been able to show that the spatial distribution of polarized scatter also changes upon particle aggregation as the particles now scatter in an increased forward direction (i.e. in the Mie limit). With an initial solution optical density of ≈1, significant depolarization occurs at angles greater than 140°, less than 220° and maximum around 180° from the incident excitation. Subsequently, this approach allows the determination of solution protein or analyte concentrations using polarized scatter, the dynamic sensing range determined by the angle of observation.

For the presently described sandwich assay sensing scheme, the initial noble metal immobilized nanostructures were chosen so that it would be in the Rayleigh limit, i.e. 20 nm. Upon receptor/ligand induced aggregation of the two metal structures at opposing ends of the receptor/ligand/detector complex, the scattering distributions become increasingly more complex as a function of ligand binding, and the scattering no longer following a Cos 2θ dependence. The polarization changes, and can subsequently be correlated with ligand concentration. Any analyte or biospecies which can induce the approach of the metallic structures to cause interaction between the structures and aggregation may be used in the present invention. Importantly, the dynamic range of the sensing strategy manifests itself in being able to aggregate particles that initially scatter in the Rayleigh limit, into the Mie limit after aggregation.

The angle-dependent long-range polarized-scattering from metallic surfaces can be measured using g using an X-Y rotating stage (Edmund Optics), that was modified to hold a cylindrical cuvette (a thin walled NMR tube), with a fiber optic mount, as shown in FIG. 1. The metallic structures can be illuminated with vertically polarized laser sources with a neutral density filter being used to adjust the laser intensity. The angle-dependent vertically polarized scattered light from the metallic surfaces can be collected through a dichroic sheet polarizer (Edmund optics) into a 600 micron broad wavelength fiber that was connected to an Ocean Optics HD2000 spectrofluorometer. The photostability aggregation of metallic surfaces can be measured by simply observing the polarized scattered intensity at different angles, such as 90 or 140 degrees for a specific length of time, such as 30 or 45 minutes.

Notably, the present invention provides for the application of plasmon scatter and the measurement of distances in the range 10-300 nm for biological systems. Today, optical distance measurements less than 10 nm are undertaken using FRET between a fluorescent donor and an acceptor. Distances ranging from macroscopic to about λ/2, typically about 300 nm, can be measured using confocal, multiphoton and/or laser scanning methods but these systems are not readily compatible with biological species, such as live cells. Thus, long-range FRET utilizing plasmonics may be possible, based on the changes in the scattering, absorption and polarization properties of suitably sized colloids. Interestingly, the coupling distance (transfer distance in FRET) is dependent on the wavelength of light and the initial choice of colloid size. This approach may be of significant importance for studying macromolecular dynamics and particularly in immunoassays, which typically have dimensions far too large for classical FRET.

Another sensing platform that is applicable to the coupling of long-range plasmonic scatter from two separate and distinct metallic surfaces that approach and interact includes wavelength ratiometric plasmon scattering. Specifically, measuring the intensity of the coupled long range scattered light from the opposing ends of the metal complex can be measured at two separated angles and determining the ratio of same. Importantly, as more receptor-ligand complexes form and formation of metal complexes increases the ratio of the scattered light at the two separate angles approaches unity as discussed previously relating to FIG. 5.

Figure 14:
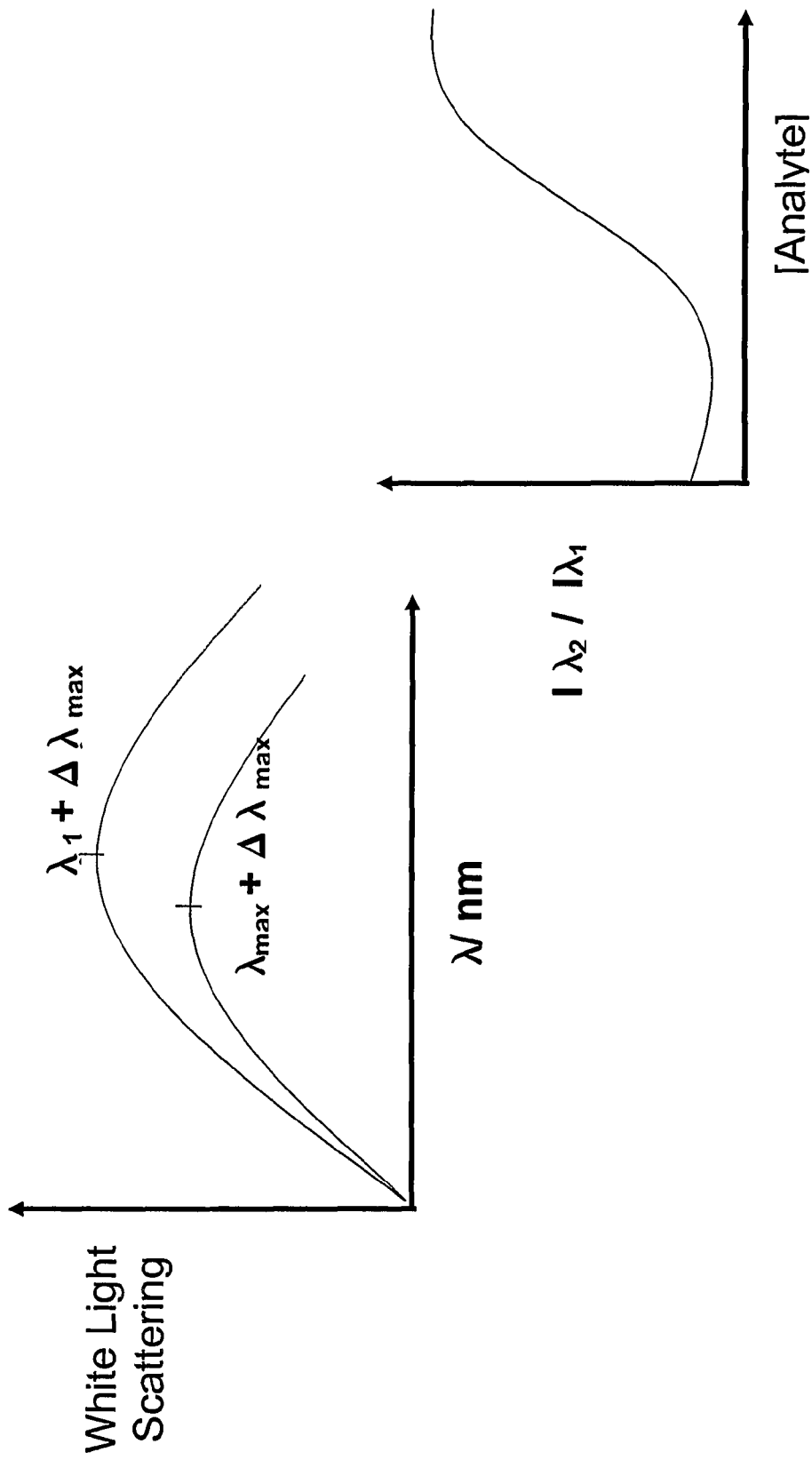
FIG. 14 shows the ratio of plasmon scattering at different wavelengths.

This approach is unique in that the measurements are independent of both excitation light fluctuations, as well as the concentration of the colloidal sensing species. As shown in FIG. 14 by exciting the surface with two different laser lines at different wavelengths, or even white light illumination, and then taking the ratio of the scattered intensities (at 2 unique wavelengths, $\lambda_1$ and $\lambda_2$) the concentration of the ligand/analyte can be ratiometrically determined.

Figure 12:
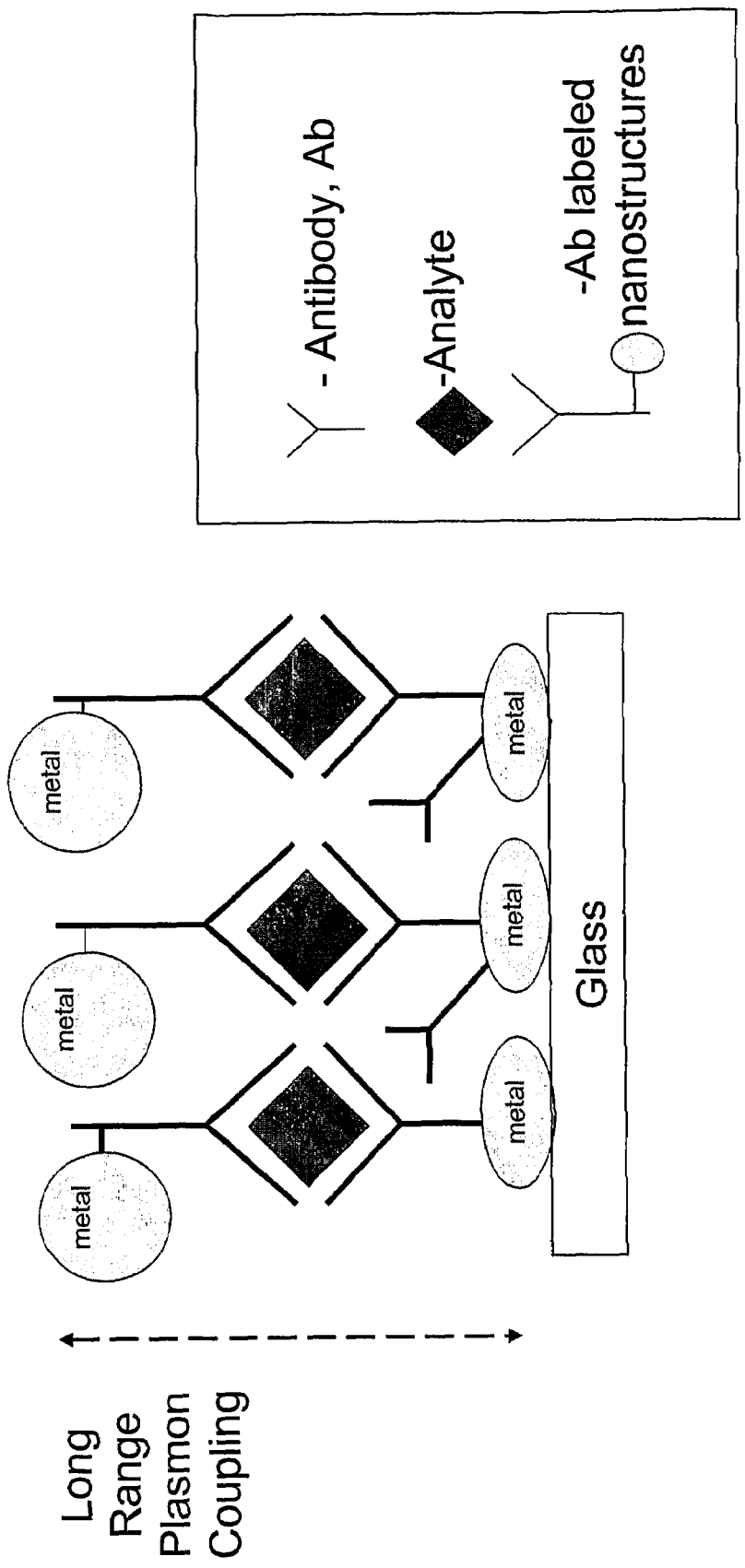
FIG. 12 shows a sandwich immunoassay of the present invention.
Figure 13:
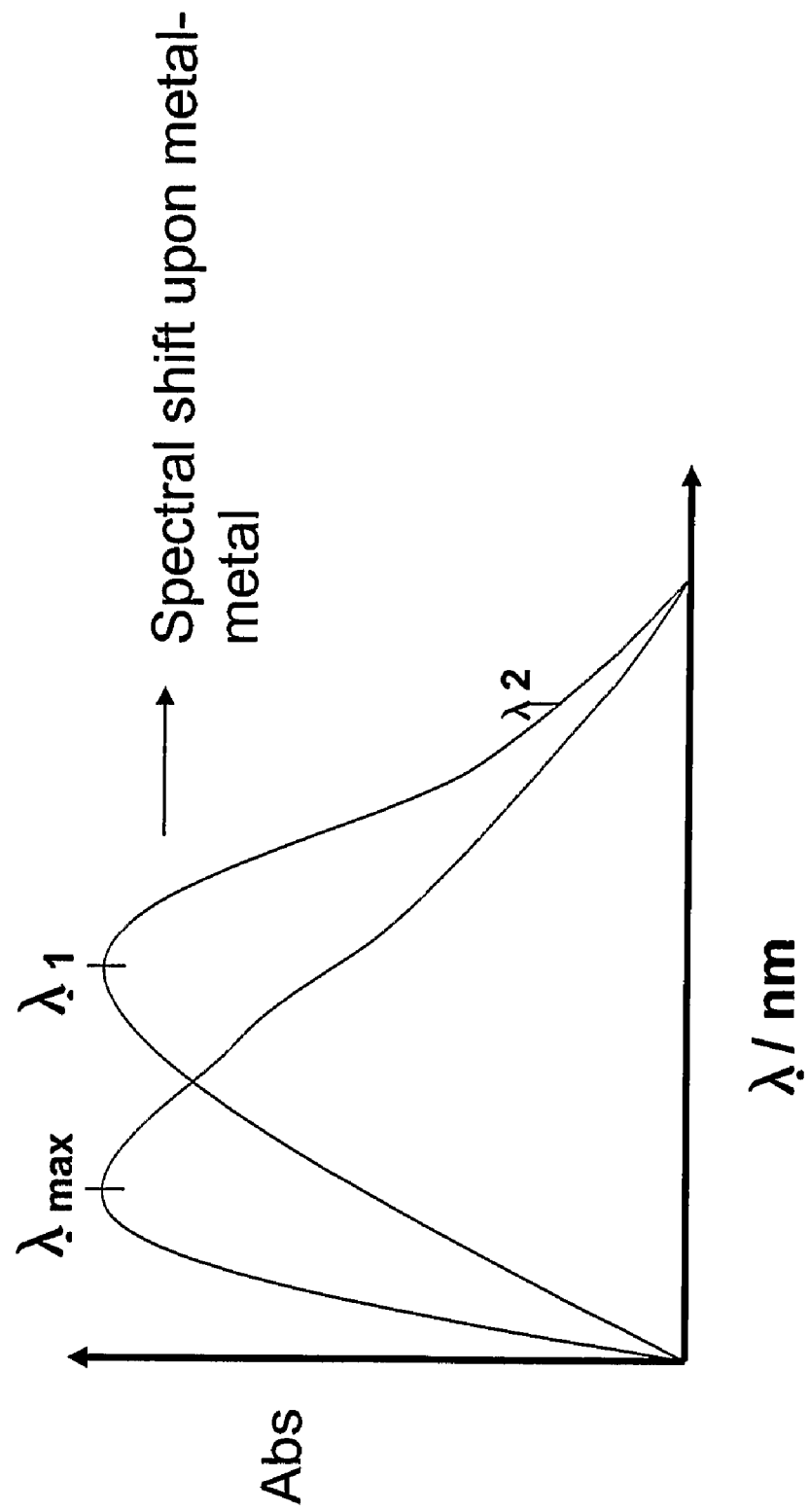
FIG. 13 shows the shift in wavelength upon metal-metal/plasmon-plasmon coupling.

FIG. 13 shows yet another sensing platform to determine the level of ligand/analyte binding. In the sandwich immunoassay shown in FIG. 12, the presence of an analyte facilitates bringing a noble-metal nanostructure in close proximity to a metallic surface. Long-range plasmon coupling occurs (up to 1000 nm), far-greater than any fluorescence based coupling (up to 10 nm max for resonance energy transfer based assays), causing a change in surface color due to the change in absorption at different wavelengths, depending on the concentration of the analyte of interest. When the analyte of interest binds to the surface antibodies as shown in FIG. 12, followed by the second antibody which is labeled with a metallic nanostructure, then a spectral shift in the absorption occurs as shown in FIG. 13.

EXAMPLE

Materials and Methods

Materials

Colloidal gold dispersions (20, 40, 100 and 200 nm) were purchased from Ted Pella. Glycerol, sodium phosphate monobasic, phosphate buffered saline (PBS), streptavidin, biotinamidocaproyl labeled bovine serum albumin (biotinylated BSA) and standard glass NMR tubes (5 mm, series 300) were purchased from Sigma-Aldrich. All chemicals were used as received.

Methods

Preparation of Biotinylated BSA-Coated 20 nm Gold Colloids

The surface modification of 20 nm gold colloids was performed using an adapted version of the procedure found in the literature.[19] In this regard, 5 mL of the gold colloid solution was mixed with 0.05 mL aqueous solution of biotinylated BSA (1.44 mg/ml), and this mixture was incubated at room temperature for 2 hours. The gold colloid/biotinylated BSA mixture was then centrifuged in an Eppendorf centrifuge tube equipped with a 100,000 MW cut-off filter for 10 minutes, using an Eppendorf microcentrifuge at 8,000 g, to separate the biotinylated BSA-coated gold colloids from the excess biotinylated BSA. The supernatant was carefully removed, and the pellet containing the biotinylated gold colloids was resuspended in 10 mM sodium phosphate buffer (pH 7). This was subsequently used in the aggregation assays.

Aggregation Assay Using Biotinylated Gold Colloids and Streptavidin

The model aggregation assay, used to demonstrate the utility of the present invention, was performed by mixing biotinylated gold colloids (20 nm) with increasing concentrations of streptavidin in a quartz cuvette. In this regard, a 1000 nM stock solution of streptavidin (prepared in PBS based on the specifications provided by manufacturer, E1% at 282 nm=31.0) was added to 0.5 mL of biotinylated gold colloid samples and incubated at room temperature for 30 minutes. In order to achieve the desired final streptavidin concentrations, predetermined volumes of streptavidin stock solution were used. The degree of aggregation was measured by recording the absorption spectrum of each sample (as with all other absorption measurements), using a Varian Cary 50 spectrophotometer.

Aggregation Assay

The angle-dependent scattering from gold colloids of various sizes and those used in the aggregation assay were measured using an X-Y rotating stage (Edmund Optics), that was modified to hold a cylindrical cuvette (a thin walled NMR tube), with a fiber optic mount (FIG. 1—bottom). The gold colloids were illuminated with three different vertically polarized laser sources: 470, 532 and 650 nm, a neutral density filter being used to adjust the laser intensity. The angle-dependent vertically polarized scattered light from the gold colloids was collected through a dichroic sheet polarizer (Edmund optics) into a 600 micron broad wavelength fiber that was connected to an Ocean Optics HD2000 spectrofluorometer. The photostability of 20, 40 and 200 nm gold colloids, under constant illumination with a 532 nm laser, was measured by simply observing the scattered intensity at 140° for 30 minutes.

REFERENCES

The contents of all cited references are hereby incorporated by reference herein for all purposes.

(1) Bryant, G.; Thomas, J. C. *Langmuir* 1995, 11, 2480-2485.
(2) Dahneke, B. E. Ed. *Measurements of Suspended Particles by Quasi-Elastic Light Scattering*, Wiley-Interscience, New York, 1983.
(3) Chu, B. *Laser Light Scattering*, 2nd Ed., Academic Press, New York, 1991.
(4) Brown, W. Ed. *Dynamic Light Scattering: The Method and Some Applications*, Clarendon Press, Oxford, England, 1993.
(5) Finay, R. *Adv. Colloid Interface Sci.* 1994, 52, 79-143.
(6) Yguerabide, J.; Yguerabide, E. *Anal. Biochem.* 1998, 262, 137-156.
(7) Yguerabide, J.; Yguerabide, E. *Anal. Biochem.* 1998, 262, 157-176.
(8) Aslan, K.; Lakowicz, J. R.; Geddes, C. D. *Anal. Chem. Acta.* 2004, 517, 139-144.
(9) Aslan, K.; Lakowicz, J. R.; Geddes, C. D. *Anal. Biochem.* 2004, 330, 145-155.
(10) Reynolds, R. A.; Mirkin, C. A.; Letsinger, R. L. *J. Am. Chem. Soc.* 2000, 122, 3795-3796.
(11) Elghanian, R.; Storhoff, J. J.; Mucic, R. C.; Letsinger, R. L.; Mirkin, C. A. *Science* 1997, 277, 1078-1081.
(12) Sastry, M.; Lala, N.; Patil, V.; Chavan, S. P.; Chittiboyina, A. G. *Langmuir* 1998, 14, 4138-4142.
(13) Cobbe, S.; Connolly, S.; Ryan, D.; Nagle, L.; Eritja, R.; Fitzmaurice, D. *J. Phys. Chem. B* 2003, 107, 470-477.
(14) Nath, N.; Chilkoti, A. *Anal. Chem.* 2002, 74, 504-509.
(15) Souza, G. R.; Miller, J. H. *J. Am. Chem. Soc.* 2001, 123, 6734-6735.
(16) Kerker, M. The Scattering of Light and Other Electromagnetic Radiation, Academic Press, New York, 1969.
(17) Mie, G, *Ann. Phys.* 1908, 25, 377-445.
(18) Collier, C. P.; Vossmeyer, T.; Heath, J. R. *Annu. Rev. Phys. Chem.* 1998, 49, 371-404
(19) Roll, D.; Malicka, J.; Gryczynski, I.; Gryczynski, Z.; Lakowicz, J. R. *Anal. Chem.* 2003, 75, 3108-3113.
(20) Mayes, A. G.; Blyth, J.; Millington, R. B.; Lowe, C. R. *Anal. Chem.* 2002, 74, 3649-3657.
(21) Kim, Y.; Johnson, R. C.; Hupp, J. T. *Nano Lett.* 2001, 1 (4), 165-167.
22) Lakowicz, J. R. Principles of Fluorescence Spectroscopy; Kluwer/Academic Plenum Publishers: New York, 1997.
(23) Millard, M.; Huang, P.; Brus, L. *Nano Lett.* 2003, 3, 1611-1615.

That which is claimed is:

1. A biosensing method for measuring concentration of an analyte that induces colloidal aggregation, the method comprising:
    (a) preparing small metallic colloids comprising a metal and at least partially coated with a binding component having an affinity for the analyte, and wherein the small metallic colloids are sized to scatter light according to the Rayleigh theory and range from 10 nm to 40 nm;
    (b) contacting the small metallic colloids with an analyte that has an affinity for the binding component to form an analyte/binding component complex, wherein the analyte has the ability to bind to multiple binding components forming aggregates of metallic colloids; and
    (c) measuring the change in intensity of scattered light from small metallic colloids relative to the intensity of scattered light measured for aggregates of metallic colloidals when exposed to electromagnetic radiation at a frequency that is absorbed and scattered, wherein the intensity of the scattered light is measured at two angles relative to the incident light and a change of the ratio is determined between the measured values at the two angles, and wherein the value of the ratio decreases as aggregation increases.

2. The method according to claim 1, wherein the analyte is an amino acid sequence or nucleotide sequence.

3. The method according to claim 1, wherein the small metallic colloids are gold or silver particles.

4. The method according to claim 1, wherein the angles for measuring intensities comprise from 40 to 160 degrees for one angle and from 200 to 320 degrees for the second angle.

5. The method according to claim 1, wherein the intensity of the scattered light from the small metallic colloids is measured before introducing the analyte and after contact with the analyte, wherein the intensity of the scattered light is measured at the same two angles.

6. The method according to claim 1, wherein the electromagnetic radiation is applied by a monochromatic laser light at a frequency similar to plasmon absorption maxima of the metallic colloids.

7. The method according to claim 1, wherein the electromagnetic radiation is applied by a monochromatic laser light at a frequency similar to plasmon absorption maxima of the metallic colloids.

* * * * *